(12) United States Patent
Bartlett et al.

(10) Patent No.: US 6,177,402 B1
(45) Date of Patent: *Jan. 23, 2001

(54) METHOD FOR REGULATING NEURON DEVELOPMENT AND MAINTENANCE

(75) Inventors: Perry Bartlett, North Carlton; Mark Murphy, Fitzroy, both of (AU)

(73) Assignee: Amrad Corporation, Ltd., Victoria (AU)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/410,402

(22) Filed: Mar. 27, 1995

Related U.S. Application Data

(63) Continuation of application No. 07/923,939, filed as application No. PCT/AU91/00103 on Mar. 20, 1991, now abandoned.

(30) Foreign Application Priority Data

Mar. 19, 1990 (AU) .................................................... PJ9205

(51) Int. Cl.⁷ ............................ A01N 37/18; A61K 38/00
(52) U.S. Cl. ................................... 514/2; 514/12
(58) Field of Search ........................................... 514/2, 12

(56) References Cited

U.S. PATENT DOCUMENTS

| | | | |
|---|---|---|---|
| 5,166,065 | * 11/1992 | Williams et al. | 435/240.1 |
| 5,187,077 | * 2/1993 | Gearing et al. | 435/69.1 |
| 5,843,892 | * 12/1998 | Patterson . | |
| 5,968,905 | * 10/1999 | Patterson . | |

FOREIGN PATENT DOCUMENTS

| | | | |
|---|---|---|---|
| 0412554 | 2/1991 | (EP) | A61K/9/22 |
| 8807548 | 10/1988 | (WO) | C07K/13/00 |
| 9002183 | 3/1990 | (WO) | C12N/15/24 |

OTHER PUBLICATIONS

Metcalf etal (1989) Proc. Nat'l Acad. Sci. 86:5948–5952.*
Murphy etal (1991) Proc. Nat'l Acad Sci 88: 3498–3501.*
Wyngaarden etal (eds) (1992) "Textbook of Medicine (19th ed.)," W.B. Saunders Co., Philadelphia, pp. 1462–1465 & 1479–1483.*

Kandel etal (eds) (1991) "Principles of Neural Science", Elsevier Science Publishing Co, Inc., New York, pp. 902–905.*

Websters II New Riverside University Dictionary (1988) Houghton Mifflin Co., p. 990.*

Moreau et al. "Leukaemia inhibitory factor is identical to the myeloid growth factor human interleukin for DA cells" *Nature* vol. 336, Dec. 15, 1988, pp. 690–692.

Yamamori et al. "The Cholinergic Neuronal Differentiation Factor from Heart Cells is Identical to Leukemia Inhibitory Factor" *Science* vol. 246, Dec. 15, 1989, pp. 1412–1416.

Fukada etal (1985) Proc.Nat'lAcad.Sci. 82:8795–8799.*

Varon etal (1984) Dev. Neurosci. 6:73–100.*

Fingl etal (1975) In "The PharmacologicalBasis of Therapeutics" (L. S. Goodman et al, eds) MacMillanPublishing Co., New York.*

Mayer et al. (1991) "Recombinant Human Leukemia Inhibitory Factor (rhLIF) is an Inductor of Acute Phase Proteins and Raises the Blood Platelets in Nonhuman Primates", *Molecular Biology of Hematopoieses*.

Cheema et al. (1993) "Leukemia Inhibitory Factor Prevents the Death of Axotomised Sensory Neurons in the Dorsal Root Ganglia of the Neonatal Rat", *Journal of Neuroscience Research 36*, 106.

Richards et al. (1992) "De Novo Generation of Neuronal Cells from the Adult Mouse Brain", *Proc. Natl. Acad. Sci. USA 89*, 8591–8595.

Yuen etal, Annals Neurol 40:346–354, 1996.*

Jackowski, British Journal of Neurosurgery, 9:303–317, 1995.*

* cited by examiner

*Primary Examiner*—Patricia A. Duffy
(74) *Attorney, Agent, or Firm*—Scully, Scott, Murphy & Presser

(57) ABSTRACT

The present invention provides methods for regulating neuron development, regeneration and maintenance by administration of leukemia inhibitory factor (LIF). Pharmaceutical compositions containing LIF and one or more additional neuron stimulating factors are also provided.

10 Claims, 16 Drawing Sheets

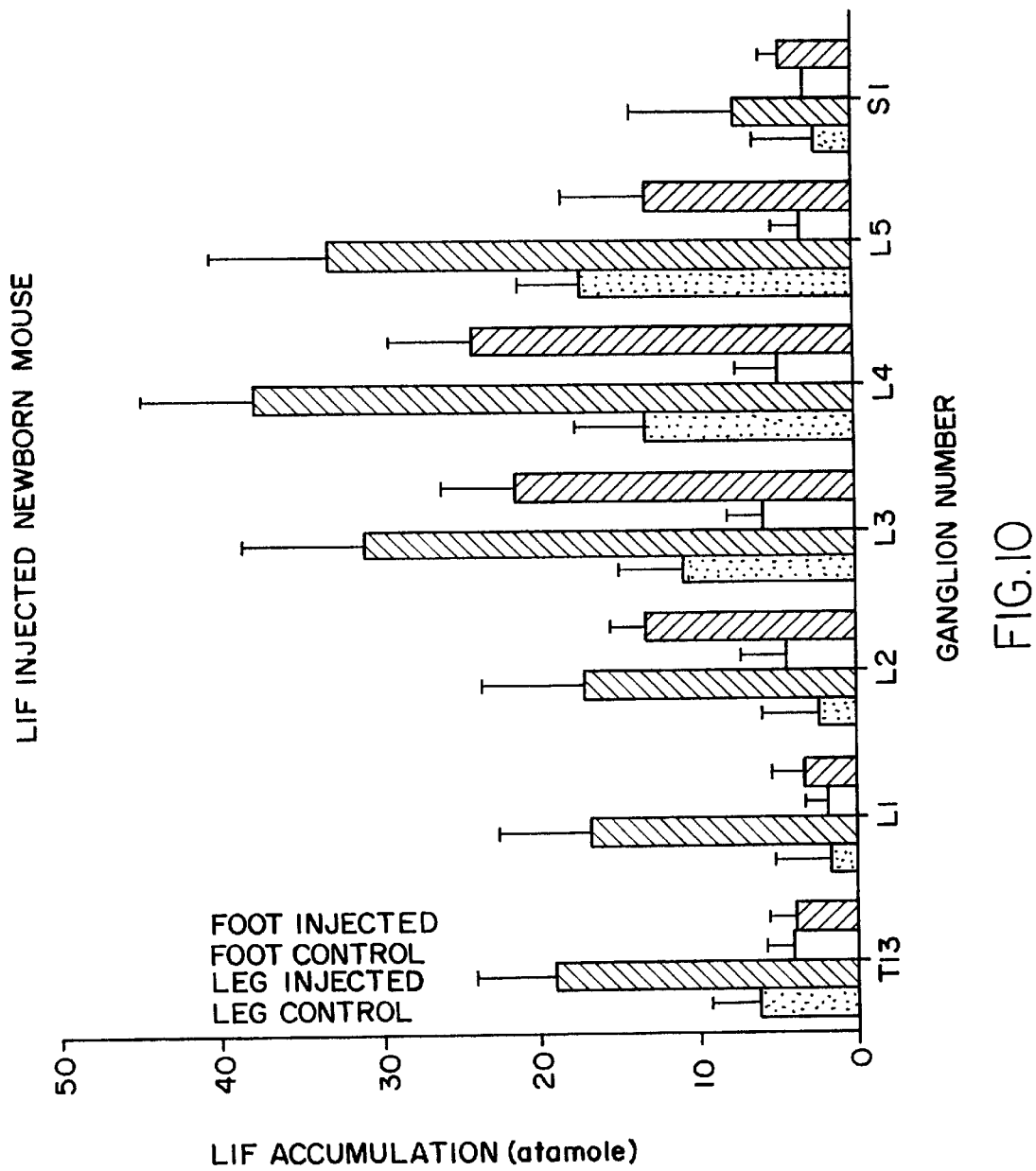

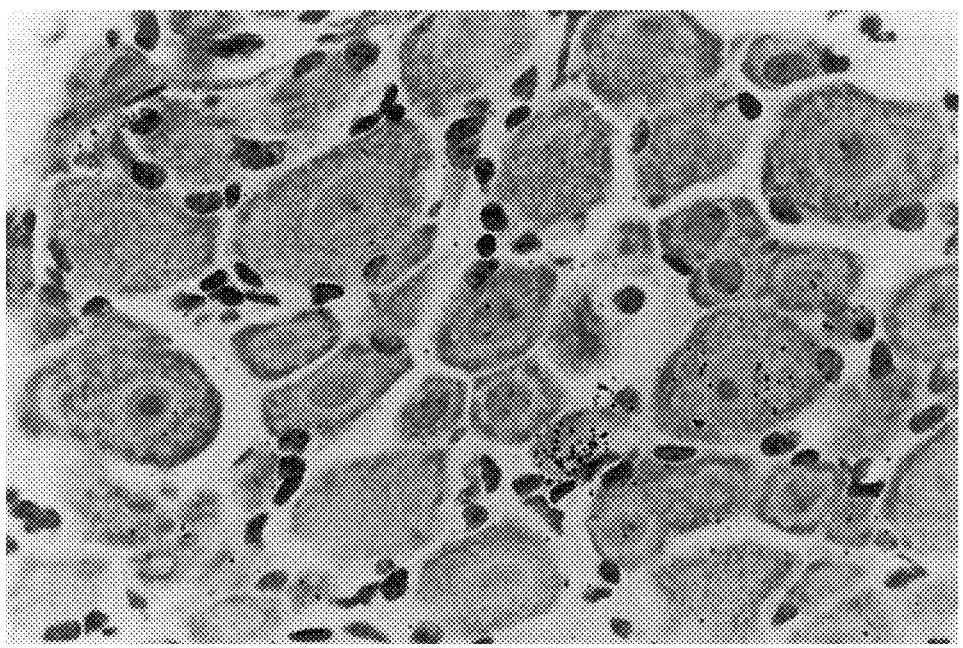
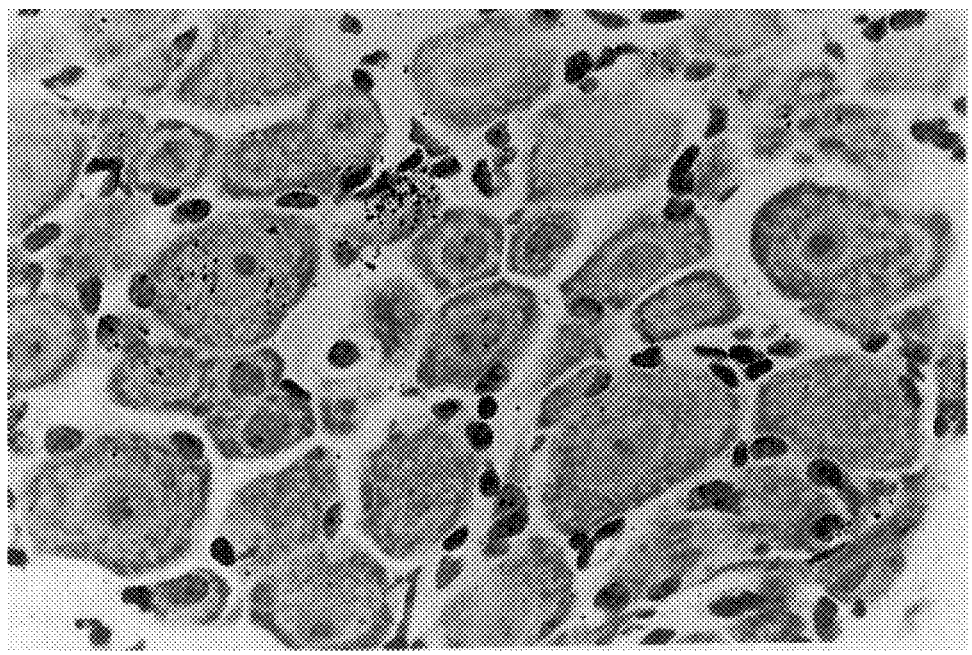
FIG.11a

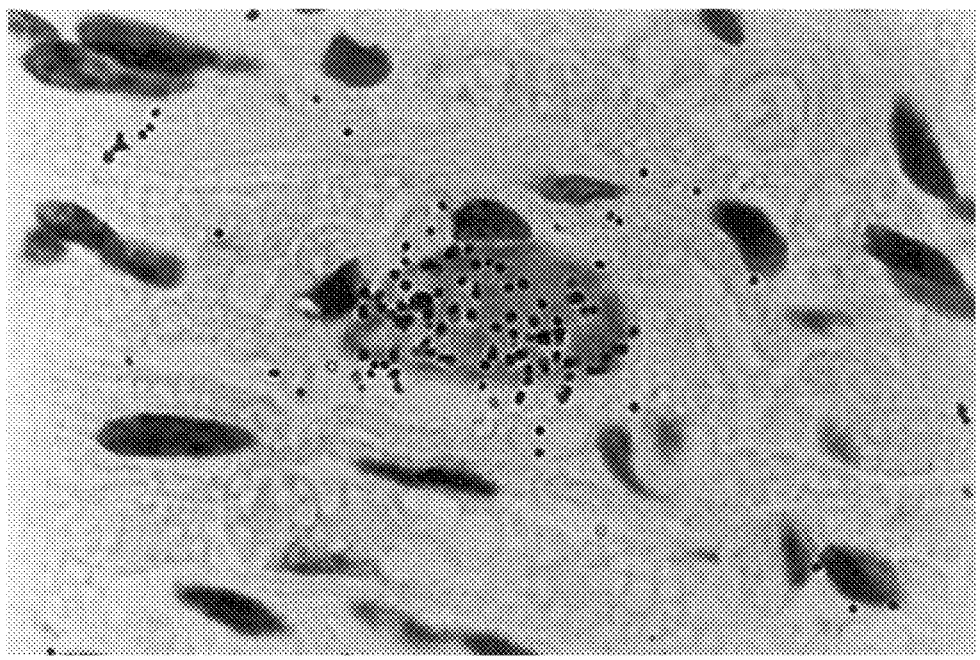
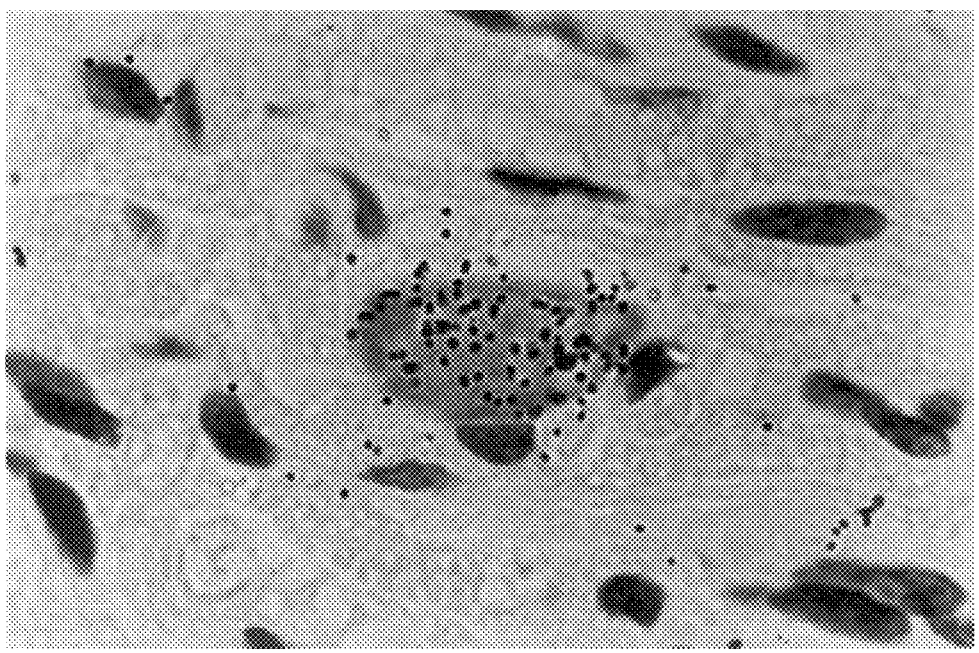
FIG.11b

METHOD FOR REGULATING NEURON DEVELOPMENT AND MAINTENANCE

This is a continuation of application Ser. No. 07/923,939 filed on Nov. 19, 1992 now abandoned corresponding to a national Stage filing of International Application PCT/AU91/00103 filed on Mar. 20, 1991 and which designated the U.S.

The present invention relates to a method for regulating neuron development, maintenance and regeneration in the central and peripheral nervous systems of a mammal and to pharmaceutical compositions comprising leukaemia inhibitory factor useful for same. The present invention is particularly useful in the treatment of developmental and cerebral anomalies and neuropathies in mammals and in particular humans.

Leukaemia Inhibitory Factor (hereinafter referred to as "LIF") is a protein that has been purified, cloned and produced in large quantities in purified recombinant form from both *Eschericia coli* and yeast cells (International Patent Application PCT/AU88/00093). LIF was originally isolated on the basis its capacity to induce differentiation and suppression of the murine myeloid leukaemic cell line, M1. LIF has no apparent proliferative effect on normal haematopoietic cells although LIF receptors have been detected on cells of the monocyte-macrophage lineage.

The present invention arose in part from an investigation of the effects of LIF on cells of the neural crest. The neural crest is a population of precursor cells which arises from the dorsal lip of the neural tube during embryogenesis and migrates through the embryo along a complex series of pathways. After migration the crest cells give rise to a great variety of cell types including the neurons and Schwann cells of the sensory and autonomic ganglia, the enteric nervous system, adrenal medulla, melanocytes of the skin and facial mesenchyme. When studied at the population level, the crest appears to be a multipotent collection of stem cells. The extensive transplantation experiments of Le Douarin and colleagues, whereby quail neural crest were grafted into chick embryos, showed that the developmental fate of the crest cells was determined by the location of this graft in the chick embryo (1). This not only indicated that the full developmental repertoire of the crest is contained in the different subpopulations of grafted crest cells, but also that environmental factors play a major role in the final differentiated phenotype of the cells.

In the last decade it has become increasingly clear that the neural crest contains subpopulations of cells which are already committed to particular developmental pathways (2,3). However, it is also clear that the differentiation of these cells is determined by environmental factors.

A number of soluble trophic factors have been shown to act as survival agents for neural crest derived neurons, but none of these have been shown to act directly on the neuronal precursor cells within the neural crest. These factors include nerve growth factor (NGF; 4), brain-derived neurotrophic factor (BDNF; 5), ciliary neurotrophic factor (CNTF; 6) and the fibroblast growth factors (FGF's; see 5).

In work leading up to the present invention, experiments were conducted to locate an agent having direct effect on the precursor populations of the neural crest. In accordance with the present invention, it has been surprisingly discovered that neural crest cells differentiate into fully mature neurons in the presence of LIF. This effect is titratable and occurs in the absence of proliferation of neuronal precursor cells. Furthermore, the effect of LIF on the differentiation of neural crest cells into neurons extends to the stimulation of the differentiation of precursor cells in embryonic dorsal root ganglia into mature sensory neurons.

Accordingly, one aspect of the present invention contemplates a method for regulating neuron development and/or maintenance and/or regeneration in a mammal comprising administering to said mammal an effective amount of leukaemia inhibitory factor (LIF) for a time and under conditions sufficient to permit the differentiation and/or maintenance and/or regeneration of neural precursor cells into neurons.

Another aspect of the present invention relates to a method for enhancing and/or stimulating and/or maintaining and/or regenerating the formation and/or survival of neurons in the central nervous system of a mammal which comprises administering to said mammal an effective amount of LIF for a time and under conditions sufficient to effect an increase in and/or to maintain the number of neurons in the central nervous system.

In one embodiment, the LIF enhances, stimulates, maintains (i.e. promotes survival) and/or regenerates immature neurons.

Yet another aspect of the present invention relates to a method for enhancing, stimulating and/or maintaining the formation and/or survival of sensory neurons, for example sensory neurons, of the peripheral nervous system of a mammal which comprises administering to said mammal an effective amount of LIF for a time and under conditions sufficient to effect an increase in and/or to maintain the number of neurons in the peripheral nervous system. By "LIF" as used herein is meant to include naturally occurring, recombinant and synthetic LIF comprising the naturally occurring amino acid sequence or any single or multiple amino acid substitutions, deletions and/or additions therein including single or multiple substitutions, deletions and/or additions to any molecules associated with LIF such as carbohydrate, lipid and/or peptide moieties. Accordingly, the term "LIF" as used herein contemplates naturally occurring LIF and LIF-like polypeptides which include mutants, derivatives, homologues and analogues of LIF. Regardless of the LIF molecule used, however, the only requirement is that it can assist in regulating neuron development and/or maintenance and/or regeneration in a mammal. In a preferred embodiment the mammal is human and the LIF is of human origin or from a different mammal but which still has activity in a human. Hence, the source of LIF and the mammal to be treated may be homologous, i.e. from the same mammal or may be heterologous, i.e. from a different mammal. In some circumstances, the mammal to be treated may itself be used to isolate the LIF for use in the method of the present invention.

By "regulating neuron development, maintenance and regeneration" as used herein is meant to include stimulating, enhancing and/or maintaining the formation and/or survival of neurons in the central and peripheral nervous systems of a mammal. It also includes the ability of said factor to assist the regeneration of properties associated with neuronal function following damage caused by disease or trauma. It is also includes stimulating, enhancing, maintaining and/or regenerating those properties associated with neurons such as, but not limited to, neurotronsmitter type, receptor type and other features associated with this phenotype. In particular, LIF has been shown herein to induce, stimulate, enhance, maintain and/or regenerate the differentiation of neural crest cells into fully mature neurons. This effect is titratable and occurs in the absence of proliferation of neuronal precursor cells. The effect of LIF also extends to the stimulation of the differentiation of precursor cells in embryonic dorsal root ganglia (DRG) into mature sensory neurons. The sensory neurons of the peripheral nervous system are derived from precursor cells in the embryonic neural crest. After crest migration, these precursor cells aggregate into the DRG and then differentiate into mature sensory neurons. The survival of sensory neurons has been shown to be dependent on two characterised growth factors, nerve growth factor (NGF) and brain derived neurotrophic factor (BDNF) and other undefined factors at critical stages during development. However, nothing is known about the identity of factors which might stimulate the differentiation of the sensory precursor cells. It was, therefore, surprisingly found in accordance with the present invention that LIF stimulated the differentiation of precursor cells in the embryonic DRG into mature sensory neurons and that LIF acted as a survival factor for these neurons throughout embryogenesis and into postnatal life.

LIF also affects the central nervous system. The early steps in the development of the central nervous system from the embryonic precursor cells of the neural tube involves expansion of the precursor population and differentiation of these cells into mature neurons and glia. This phase is followed by a selective survival of neurons which have appropriately innervated the correct targets and is believed to be based on the limited availability of survival factors which are produced by the target cells.

It has been recently shown (9) that the fibroblast growth factors are involved in the expansion and differentiation phases of development of the embryonic brain and in addition it has also been shown that FGF can act as a survival agent for mature neurons. Work from Barde (5) indicates that the survival of a subset of CNS neurons, the retinal ganglion cells, is dependent on BDNF. However, little is known about other factors which are operative in the development of the embryonic brain and spinal cord.

Accordingly, it has now been surprisingly found that LIF acts as a differentiation/survival and/or regenerating agent for spinal cord neurons and enhances, stimulates and/or promotes spinal cord development and promotes neurite extension.

This method is particularly applicable to regulating spinal cord development and in treating a disease, injury and/or an abnormality to a nervous system. For example, the method of the present invention can be used in relation to the central and/or peripheral nervous system to treat one or more of Cerebral Palsy, trauma induced paralysis, vascular ischaemia associated with stroke, neuronal tumours, motorneurone disease, Parkinson's disease, Huntington's disease, Alzheimer's disease, multiple sclerosis, peripheral neuropathies associated with diabetes, heavy metal or alcohol toxicity, renal failure and/or infectious diseases such as herpes, rubella, measles, chicken pox, HIV and/or HTLV-1.

Another aspect of the invention relates to a method for enhancing, stimulating, maintaining and/or regenerating spinal cord development and spinal cord neuron number which comprises administering to said mammal an effective amount of LIF for a time and under conditions sufficient to effect an increase in spinal cord neuron number and spinal cord development.

Yet another aspect relates to a method of enhancing, stimulating, maintaining and/or regenerating neurite extension from spinal cord and other central nervous system neurons and further relates to the central nervous system other than the spinal cord.

Still yet another aspect of the invention contemplates a method of treatment of disease and injury in both the central and peripheral nervous systems in a mammal, said disease or injury including but not limited to one or more of Cerebral Palsy, trauma induced paralysis, vascular ischaemia associated with stroke, neuronal tumours, motorneurone disease, Parkinson's disease, Huntington's disease, Alzheimer's disease, multiple sclerosis and peripheral neuropathies associated with diabetes, heavy metal or alcohol toxicity, renal failure and/or infectious diseases such as herpes, rubella, measles, chicken pox, HIV and/or HTLV-1 which comprises administering to said mammal an effective amount of LIF for a time and under conditions sufficient to ameliorate the disease or injury.

In all such methods of the present invention, the enhancing, stimulating, maintaining and/or regenerating of neurons is referred to as "regulating neuron development". Furthermore, use of the term "LIF" includes LIF-like polypeptides and derivatives thereof as discussed above.

The effective amount of LIF used in accordance with the present invention will be that required to regulate the neurons and will generally be from about 0.01 to about 10,000 microgram ($\mu$g) per kilogram (kg) of body weight and preferably 0.1 to 10,000 $\mu$g/kg and most preferably 1 to 1000 $\mu$g/kg of body weight. However, depending on such factors as the disease treated, the treatment and the patient, more or less LIF may be used while still being within the scope of the present invention. Furthermore, it may be convenience to determine the effective amount of LIF in Units/ml or Units/kg. The definition of a Unit of LIF activity can be found in PCT/AU88/00093. For example, and not by way of limitation LIF may be used from 10 to $10^8$ U/ml. Administration may be per hour, per day, per week or per month or may be a single administration. Administration may also need to be continuous infusion.

In accordance with the present invention, LIF may be administered alone or in combination with one or more other neuron stimulating factors such as, but not limited to, FGF, CNTF and/or BDNF and/or other neurotrophic factors. In "combination" means either the simultaneous addition of LIF and the one or more other factors in the same composition or the sequential addition of the LIF and one or more other factors where a first factor is given followed by a second factor. The exact order of addition and time between additions is best determined by the practicing physician and may depend on the patient and/or the treatment required.

Accordingly, the one or more other neuron stimulating factors may be given by simultaneous or sequential administration with LIF. The effective amount of other neuron stimulating factors will be from about 0.01 to about 10,000 $\mu$g/kg body weight, preferably 0.1 to 10,000 $\mu$g/kg and most preferably 1 to 1,000 $\mu$g/kg body weight. Again, administration may be a single dose or repeated per hour, per day, per week or per month. Administration may also be continuous infusion.

The route of administration is preferably by intramuscular or intravenous injection or using gene therapy although other routes of administration are possible such as by infusion, drip, intracerebral injection and/or implants.

Another aspect of this invention relates to administration of LIF to target tissue, or the precise location of the nerve so as to facilitate uptake by retrograde transport as outlined in Example 5.

The present invention is also directed to a pharmaceutical composition comprising LIF and one or more neuron stimulating factors and one or more pharmaceutically acceptable carriers and/or diluents. Such a composition is useful for regulating neuron development and/or maintenance in a mammal such as in enhancing, stimulating, maintaining and/or regenerating the formation and survival of neurons in the peripheral nervous system and/or enhancing, stimulating, maintaining and/or regenerating the formation and survival of sensory neurons in the central nervous system and/or enhancing, stimulating and/or maintaining the formation and survival of spinal cord neurons and/or spinal cord development.

Preferably, the composition is suitable for administration into a human. In accordance with the present invention, the LIF used in the composition is as previously herein defined and includes, for example, LIF-like polypeptides and mutants, derivatives, homologues and/or analogues of LIF. The LIF and other neuron stimulating molecules and/or neurotrophic factors may be the same or different in terms of their mammalian source and whether they are naturally occurring, recombinant or synthetic. As with the method, the mammalian source of the LIF and other neuron stimulating factor may be homologous or heterologous to the mammal being treated. The compositions of the present invention are also useful in treating the diseases, injuries and/or abnormalities of a nervous system as previously described.

The preparation of pharmaceutical compositions is well known in the art and reference can conveniently be made to *Remington's Pharmaceutical Sciences*, 16th ed., 1980, Mach Publishing Co., Edited by Osol et al.

Another aspect of the present invention is directed to the use of LIF including its derivatives for the manufacture of a medicament for enhancing, stimulating, maintaining and/or regenerating the formation and/or survival of neurons in the peripheral nervous system and/or enhancing, stimulating maintaining and/or regenerating the formation and/or survival of neurons in the central nervous system and/or enhancing, stimulating, maintaining and/or regenerating the formation and/or survival of spinal cord neurons and/or spinal cord development in a mammal. Preferably, the mammal is a human and the LIF used is as hereinbefore defined. The use in accordance with the present invention may also include the use of one or more other neuron stimulating factors such as FGF, CNTF and/or BNDF.

The present invention is further described by reference to the following non-limiting figures and examples.

In the Figures:

FIG. 1 shows the effect of LIF on neuron numbers in neural crest cultures. Neural crest cells were incubated in medium alone or in the presence of LIF for 6 days, Nissl stained (8), and neurons were counted using bright field microscopy. In the "—tube" experiment, neural tubes were removed after 24 h and LIF was added to the cultures. Neuron numbers could not be accurately counted at later times because of dense clustering of neurons in LIF cultures. Numbers are the mean and standard deviation, n=6. *$P<0.005$, **$P<0.05$; t-test.

FIGS. 2a–2g are a photographic representation showing the phenotype of neurons in neural crest cultures. Neural crest cultures were incubated for 13 days in the presence (b,d,e,f,g) or absence of LIF (a,c). Photomicrographs shown are: a, b, bright field views of Nissl stained (8) cultures; c,d, fluorescence views of cultures stained for neurofilament. e, bright field view of LIF treated culture stained for calcitorem gene related peptide (CGRP). f, bright field view of LIF treated culture stained for tyrosine hydroxylase. g, fluorescence view of same field as in (f). bar=200 $\mu$m (a,b), 50 $\mu$m (c,d,e,f,g).

FIGS. 3a–3b are a photographic representation showing $^3$H-thymidine incorporation into neural crest cultures. $^3$H-thymidine (0.03 $\mu$C/ml) and LIF ($10^4$ U/ml) were added after 4 days of culture and incubation continued for another 9 days, following which cultures were stained for neurofilament and autoradiographed (9). a, bright field photomicrograph of culture; b, fluorescence view of same field. bar=50 $\mu$m.

FIGS. 4a–4c contain graphical representations showing: A the effect of LIF on neuron numbers in cultures of E12-P2 DRG. DRG cells were plated in Monomed medium, 10% FBS (control, black bars) or +LIF ($10^4$ U/ml, hatched bars) and neuron numbers determined after 5 days (E12) or 2 days (other cultures) as described in Example 1. Numbers of neurons and cells initially plated are given in Example 1; B, limit dilution analysis of neuron survival in P2 DRG cultures. Cells (70% neurons, of which 75% plated after 2 hrs) were plated at the indicated number (120 wells/dilution) in the presence (diamonds) or absence (squares) or $10^2$ U/ml LIF and wells with live neurons were counted after 2 days. A linear relationship exists between input cells number and the log of the % negative wells (R-0.992), indicating that the effect of LIF on neuron survival obeys zero order (single hit) kinetics (11); C, dose-response relationship of neurons to LIF concentration in P2 DRG cultures. P2 DRG cells (200/well) were plated with the indicated concentration of LIF and neurons were counted after 2 days. Mean and standard deviation are shown in A and C. n-6

FIGS. 5a–5b are a photographic representation showing photomicrographs of explants of E10 spinal cords cultured in the presence of LIF in 24 well plates at D7 in vitro to display process outgrowth. Shown are cultures with a) no LIF b) LIF (Bar=100 um).

FIGS. 6 a,b are photographic representations showing the morphology of cultures arising from LIF stimulated spinal cord cells. Cells in suspension were plated as described in Example 1 and incubated in 96 well plates for 5 days. Shown are phase-contrast photographs of cells incubated with a) no LIF b) LIF (Bar=100 um).

FIGS. 6 c,d are photographic representations showing cultures of spinal cord precursors stained for neurofilament antibody. Cells were plated as described in Example 1 and incubated in HL-A plates for 5 days prior to fixation and staining. Shown are fluorescence photomicrographs of cells incubated with c) no LIF d) LIF (Bar=100 um).

FIG. 7 is a graphical representation showing the effect of LIF on process outgrowht. E10 spinal cord precursors ($5\times10^4$) were plated in the presence or absence of LIF ($10^4$ U/ml) in 96 well plates for 5 days, as described in materials and methods. The number of processes emanating from each discrete clump of cells to aggregate, was quantitated. The frequency of clumps with a given number of processes was determined. The frequencies for every 5 increments of processes/clump (e.g. 0–4, 5–9) were aggregated and expressed as a % of the total number of clumps per well. These frequencies were averaged for six wells in both LIF treated and control cultures and the means and standard deviations are expressed in the graph.

FIGS. 8a–8b are a graphical representation showing binding of $^{125}$I-LIF to sensory neurons from dorsal root ganglion. Binding (solid bars) is almost exclusively restricted to neurons as shown in (B) and not accessory cells (A). Virtually all the binding is inhibitible by cold LIF (hatched bars) indicating that binding is specific.

FIG. 9 is a graphical representation showing retrograde Transport of $^{125}$I-LIF by Sciatic Nerve in the adult mouse. Significant accumulation is found in L3, L4, L5 dorsal root ganglia when injections are made into the foot pad (solid bars).

FIG. 10 is a graphical representation showing retrograde Transport of $^{125}$I-LIF to the Sensory Ganglia in the newborn mouse. Significant accumulation of label again centred on L4 although this occurred with both foot and muscle injection. There was some uptake by more rostral sensory ganglia when injections were made intramuscularly.

FIGS. 11a–11b are a photographical representation showing an autoradiograph of section through L4 dorsal root ganglia showing accumulation of silver grains over a small population of neurons (a)×400. Note that only the neurons label, not the Schwann cells (accessory cells) (b)×1000. Sections stained with haematoxylin and eosin.

EXAMPLE 1

Materials and Methods

Preparation of Neural Crest Cells

Figure 1:
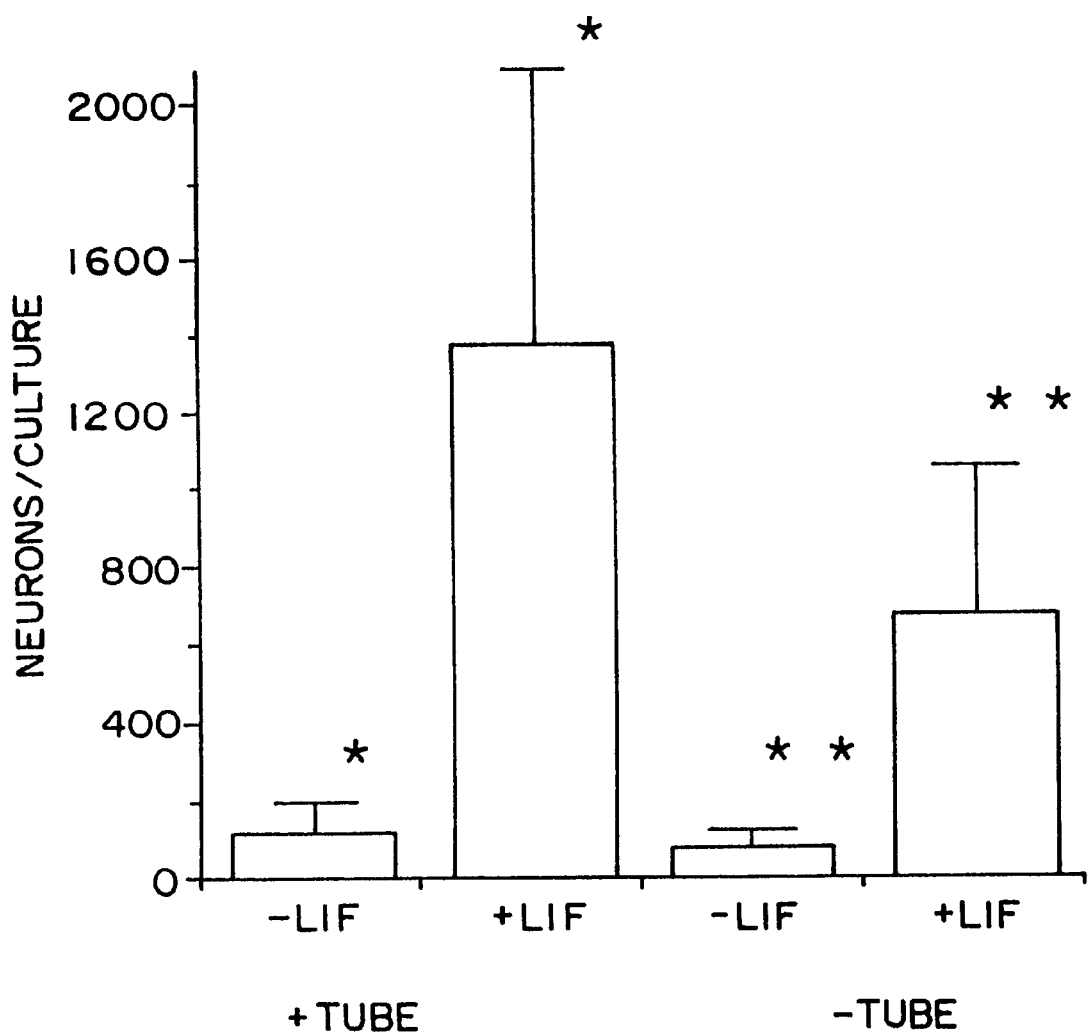

CBA mouse embryos at embryonic day 9 (E9) were removed from the uterus and placed in a petri dish containing Hepes buffered Eagles Medium (HEM) with 1% (v/v) fetal bovine serum (FBS). The head and tail were removed using 26 gauge syringe needles with the aid of a dissecting microscope leaving a trunk segment with 8–12 somites each side of the neural tube. These trunk segments were placed in a fresh petri dish in HEM 1% (v/v) FBS and the somites and surrounding tissue were carefully removed from the neural tube using 26 gauge needles. One or two tubes were then placed in each well of a 24 well plate (Linbro) which had been previously coated with fibronectin (5 ug/ml). Dulbecco's modified Eagles' medium (DME) with 10% (v/v) FBS was then carefully run down the side of each well, so that it almost covered the bottom of the well. This enabled the neural tubes to associate with the fibronectin substratum and adhere. In particular experiments, the tubes were carefully removed after 24 hrs, leaving a layer of migratory neural crest cells. In other experiments the tubes were left in the wells so as not to disturb any of the integrated crest cells. Monomed medium (Commonwealth Serum Laboratories, Parkville, Victoria, Australia) with 10% (v/v) FBS and the specified growth factors was added to 1 ml to all cultures after 24 hrs. Cultures were incubated at 37° C. in 5% $CO_2$/95% air.

Removal of Dorsal Root Ganglia (DRG)

Two day old neonatal mice were decapitated under aseptic conditions and placed into sterile petri dishes. The trunk was washed with a solution of 70% (v/v) ethanol in distilled water. A vertical incision through the skin was made using a sterile pair of 45° angle bladed scissors. All instruments used had previously been soaked for one hour before use in a solution of 70% (v/v) ethanol in distilled water.

A fine pair of iris scissors was used to make an incision through the dorsal aspect of the spinal column, which enabled the spinal cord to be removed using a pair of curved watchmaker forceps. This exposed the dorsal root ganglia and facilitated their removal. A sterile piece of gauze was used to swab the area around the ganglia so as to adsorb any blood and tissue fluid that obscured the view of the ganglia. Then using a pair of straight very fine tipped forceps each ganglia was carefully removed free of surrounding spinal tissue and placed into a petri dish in a small volume of N-2 hydroxyethylpiperasine-N-20 ethanesulfonic acid (HEPES) and buffered Eagles minimal essential medium (HEM). Approximately twenty ganglia were removed from each mouse.

DRG Cultures

The DRG dissected free of surrounding spinal tissue and placed in HEM, were finely chopped, then incubated in HEM, 0.025% (w/v) trypsin, 0.001% (w/v) DNase at 37° C. (12 min for E12, 20 min for E15 and 30 min for E19 and postnatal day 2 (P2)). FBS was added to 20% (v/v), the cells were centrifuged at 300 g for 5 min, washed twice in HEM, 0.01 (w/v) DNAse and triturated through 18–25 gauge needles to obtain a single cell suspension. DRG cells were plated onto fibronectin coated (15 μg/ml) wells of HL-A plates (Nunc, II) at previously optimised cell numbers (3500 cells at E12, 1000 at E15, and 200 at E19 and P2). Two hrs after plating, no mature neurons were observed in the E12 cultures and an average of 110, 120 and 100 neurons had were present in the E15, E19 and P2 cultures, respectively. Cultures from E12 were fixed and stained for neurofilament after 5 days and neurofilament positive neurons counted using fluorescence microscopy. Neurons in later embryonic cultures (large, phase bright, round cells) were counted after 2 days.

Immunohistochemistry

For staining with particular antibodies neural tubes were plated onto glass coverslips in 24 well plates or onto plastic microscopic slides (Nunc, 2 chamber slides). For staining with antibodies to neurofilament, the cells were first fixed in methanol at -20° C., washed 3 times in PBS and incubated for 30 min with an anti-neurofilament antibody (Chemicon) diluted 1:10 in HEM, 1% (v/v) FBS. The wells were then washed and incubated with a fluorescein isothiocyanate conjugated FITC sheep anti-rabbit antibody (Silenus) diluted 1:50 in PBS 1% (v/v) FBS, washed in PBS then in water, air dried and the cover slips mounted in 2.6% 1,4 Diazobicyclo (2,2,2) octane in PBS/glycerol (1:9) Merck, Aust. To stain for calcitonin gene related peptide (CGRP), cultures were fixed in paraformaldehyde (PFA), cleared with DMSO, washed with PBS, incubated with a rabbit anti-rat α-CGRP antibody (obtained from Dr G Olley, Monash University, Aust., and which shows 7% binding to B-CGRP, <0.01% binding to calcitonin, and negligible binding to substance P, Neurokinin A or Enkephalines by radio-immunoassay), washed and antibody binding detected using biotin conjugated second antibodies, a biotin-avidin-horseradish peroxidase complex (Vectastain ABC) and development with diamino-benzidine. To stain for tyrosine hydroxylase or choline acetyl transferase (ChAT), cultures were fixed in PFA (and picric acid for CHAT) incubated with a rabbit anti-tyrosine hydroxylase antibody (Eugene Tech. USA) or a rat antiserum prepared against porcine CHAT (which recognises ChAT in the PNS.(12), respectively and binding was detected with fluoresceinated second antibodies.

Thymidine Incorporation Experiments

To look for proliferating neural crest cells, $^3$H-thymidine (Amersham, specific activity $10^3$ Ci/mmol) was added to the cultures at 0.1 or 0.03 uCi/ml at the same time as growth factors were added or at corresponding times in control cultures. After 13 days some cultures were fixed in methanol, stained for neurofilament as described above and then dipped in Kodak NT-B2 emulsion and exposed for 2 weeks at 4° C. and then developed.

Isolation of Spinal Cord Cells

Embryos were obtained from embryonic day 10 (E10) mice. The heads were removed and the caudal part of the neural tube, or embryonic spinal cord, which forms a closed tube by E10, was removed together with the surrounding somites from the remainder of the embryo. The section of the cord used in all experiments extended from the otic vesicle to just below the developing hind limb. This tissue was subsequently incubated in Dispase II (Boehringer) in HEPES-buffered Eagle's medium (HEM) for 15 minutes at 4° C. and for 6 minutes at 37° C. The tissue was then transferred to HEM containing 1.0 (w/v) fetal bovine serum (FBS) and 0.001% (w/v) DNase and the spinal cord was dissected free of the surrounding ectoderm, somites and meninges, using the tissue plate created by Dispase incubation essentially as described previously for the preparation of the mesencephalic and telencephalic regions of the neural tube (9). Inspection at this stage revealed clean spinal cords free of contaminating mesoderm. These cords were plated directly for explant cultures into 24 well plates (Linbro). For preparation of dissociated cell suspensions, the spinal cords were then incubated at 37° C. in Hank's with 0.02% (w/v) EDTA, 10 mM Hepes, 0.025% (w/v) trypsin and 0.001% (w/v) DNase pH7.6 for 12 minutes. The reaction was stopped by the addition of FBS, the cells were washed in $Ca^{2+}/Mg^{2+}$ free Hank's and single cells were prepared by gently triturating the suspension. An average of $1.5 \times 10^5$ cells were obtained from the dissection of each embryo.

Primary Culture of Dissociated Spinal Cord Cells

Spinal cord cells ($5 \times 10^4$) were plated into 96 well plates (Linbro) coated with fibronectin (50 µg/ml) in Monomed medium and 0.05% FBS in a final volume of 100 µl. Except where otherwise stated, LIF (murine recombinant, specific activity+$10^8$U/mg) was used at a concentration of $10^4$ Units/ml. Assays were normally performed over 5 days after which the cultures began to deteriorate. Cell counts were performed after harvesting the cells with trypsin and triturating them. Process outgrowth was quantitated at day 5 by scoring the number of processes emanating from each discrete clump of cells. Numbers in all cases are the mean and standard deviation of six determinations. Cells were also plated onto confluent, irradiated (4000 Rad) monolayers of Balb/c-3T3 cells on glass microscope slides in 24 well plates in Monomed medium and 0.05% (v/v) FBS, at a density of $5 \times 10^3$ cells/well. At the specified periods of time, coverslips were fixed and stained for neurofilament as described below and the number of positively stained cells per slide was quantitated.

Purification of Radioiodination of LIF and FGF

Recombinant LIF was produced in *E. coli* as a non-glycosylated protein. The purified species electrophoresed with an apparent molecular weight of 20,000 and an isoelectric point of greater than 9.0. Iodination of LIF was performed by the iodine monochloride method as previously described (18). Briefly, 6 µl of a 1 mg/ml solution of LIF in 40% (v/v) acetonitrile, 0.1% (v/v) trifluoroacetic acid and 0.02% (v/v) Tween 20 was iodinated by addition of 1 mCi $Na^{125}I$ (New England Nuclear, North Ryde, NSW, Australia), 40 µl of 200 mM sodium phosphate, 0.02% (v/v) Tween 20 at pH 7.4 (PBS) and, while vortex mixing, 5 µl of 200 µl of ICl in 2M NaCl. After 1 min at room temperature radioiodinated LIF ($^{125}I$-LIF) was separated from unincorporated 125I by sequential gel filtration and cation-exchange chromatography. $^{125}I$-LIF produced in this manner retained full biological activity, was more than 99% precipitable with cold 20% (w/v) trichloracetic acid and greater than 90% of the radioactivity was capable of binding specifically to Ml cells (17). The specific radioactivity was $1.1 \times 10^6$ cpm/mole, as determined by self-displacement analyses. $I^{125}$ labelled aFGF was obtained as a gift from the RCC (Amersham). The specific activity of aFGF was 800 Ci/mM.

Binding Experiments and Autoradiography

Dorsal root ganglion cells were obtained from postnatal day 2 mice as described above and were cultured in 8 well microscope slides (Nunc) in monomed medium containing 10% (v/v) FCS, but no added growth factors overnight in a humidified incubator at 37° C. The slides were incubated on ice for 2 hours in 200 µl of Hepes buffered RPMI-1640 medium, supplemented with 10%(v/v) FCS, 20 µl of with or without 10 µg/ml of unlabelled LIF and from $5 \times 10^4$ cpm of $^{125}I$-LIF in 20 µl of DME, 10% (v/v) FCS. The cells were washed three times with 300 µl of PBS and fixed in 10% (v/v) formalin in PBS for 2 hours and then rinsed in water. Slides were dipped in Kodak NTB2 photographic emulsion at 42° C. in a darkroom and allowed to dry. Slides were then sealed in a light-proof box containing Drierite and exposed for 2–8 weeks at 4° C. Prior to development, slides were warmed to room temperature and developed for 3 minutes in Kodak D19 developer (40 g/500 ml of water), washed for 1 minute in 0.5%(v/v) acetic acid in water and fixed in Agfa G333c X-ray fixer for 3 minutes. Slides with cytospin preparations were stained in 5% (v/v) filter Giemsa in water for 10 minutes, dried and mounted in Depex. DePeX (BDH, Melbourne, Australia). Autoradiographs were examined at ×400, ×650, or ×1000 magnification and where necessary, grain counts were performed on 100 consecutive cells of each type and background counts, in general between 0–3 grains, were subtracted.

Retrograde Labelling Experiments

The sciatic nerves of newborn and adult Balb/C mice were ligated on one side using 6-0 prolene monofilament (Ethicon). The radioactive proteins were then injected either into the skin of the foot or intramuscularly into the centre of the gastronemus muscle. After appropriate times the animals were killed by ether overdose and the sciative nerves dissected. The nerves were cut at the ligation and 2 mm pieces were taken immediately proximal and distal to the cut and counted directly.

Newborn and adult mice were injected in the footpad and kept for 16 hours. Ganglia from T13 to S1 were removed under a disecting microscope and the radioactivity estimated in the whole ganglion in a gamma counter. Selected ganglia or spinal cords with attached ganglia were dissected from the animals and fixed in 4% paraformaldehyde in PBS prior to being embedded in emulsion. Autoradiographs were developed 3–4 weeks later and ganglia and spinal cord examined for labelled cells.

EXAMPLE 2

Effect of LIF on Neural Crest Cells and Sensory Neurons

Figure 2A:
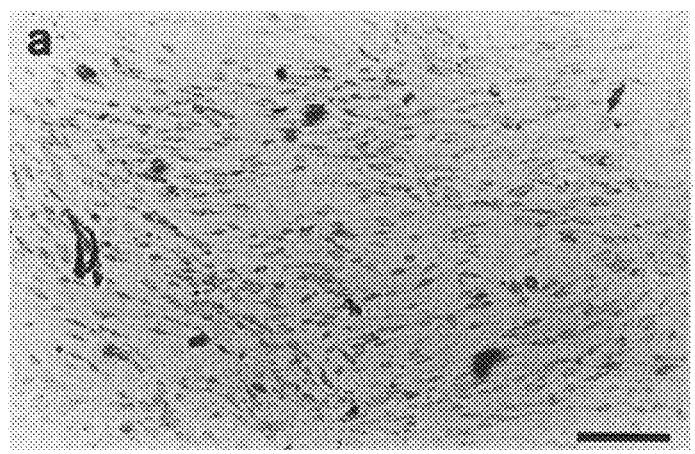
Figure 2B:
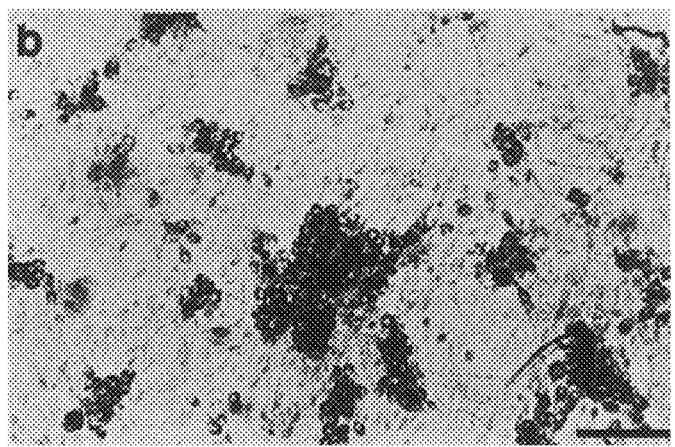
Figure 2C:
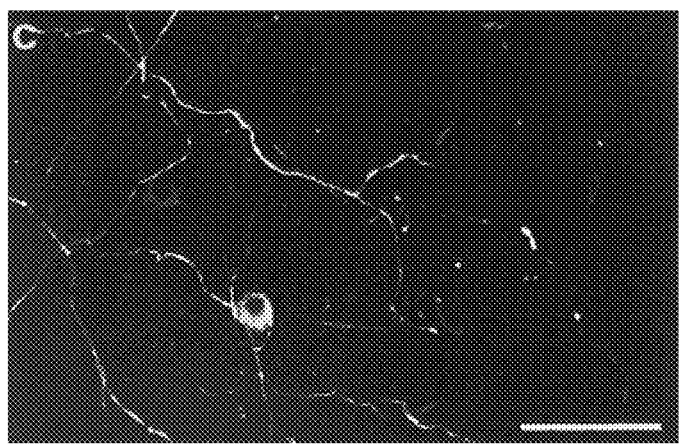
Figure 2D:
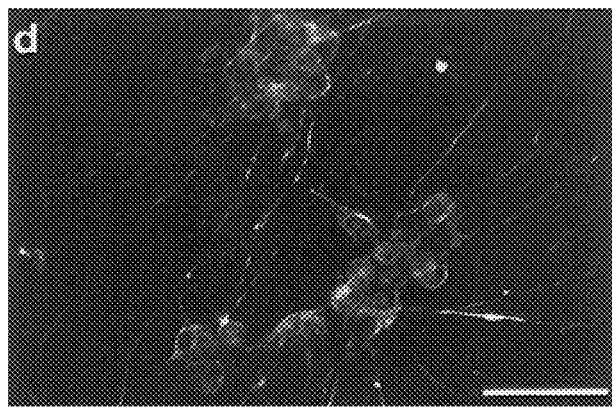

To examine the effect of LIF on neural crest cells, neural tubes were dissected from the cervical and thoracic region of E9 CBA mice, plated onto fibronectin coated wells and neural crest cells were allowed to migrate onto the substratum for 24 hr, at which time the neural tubes were either removed or left in place and LIF was added to the cultures. After two days, round cells with uni- or bi-polar processes, resembling sensory neurons, appeared in the cultures. In the LIF treated cultures there were approximately 12 fold more of these cells than in controls by 6 days (FIG. 1) and they formed large clusters which increased in size up to 14 days (FIG. 2b). This was not dependent on the presence of the neural tube during the culture period although, in their absence, the absolute number of neuron-like cells was smaller (FIG. 1). These neuron-like cells stained positively with the Nissl stain (8), (FIGS. 2a and b) and for 150 kD neurofilament (13), (FIGS. 2c and d). This staining showed fine processes emanating from the clusters (FIG. 2d), confirming their neuronal phenotype. While the effect of LIF was greatest when added at day 1, it was still apparent when added at day 7.

Figure 2E:
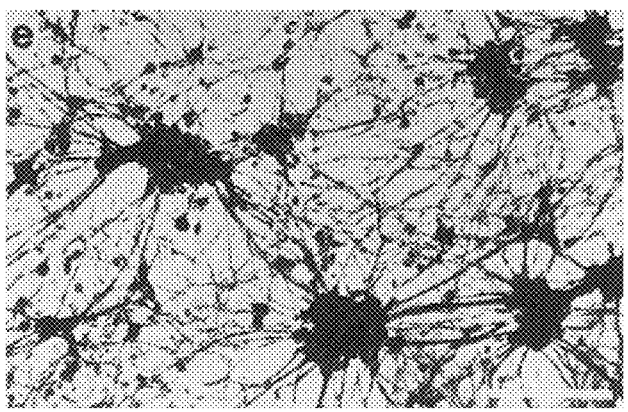
Figure 2F:
Figure 2G:
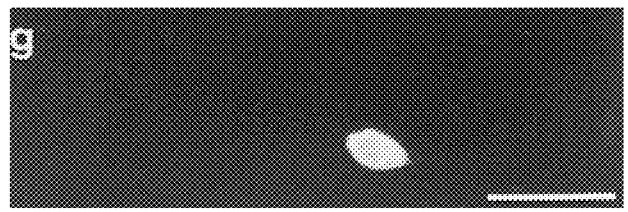
Figure 12:
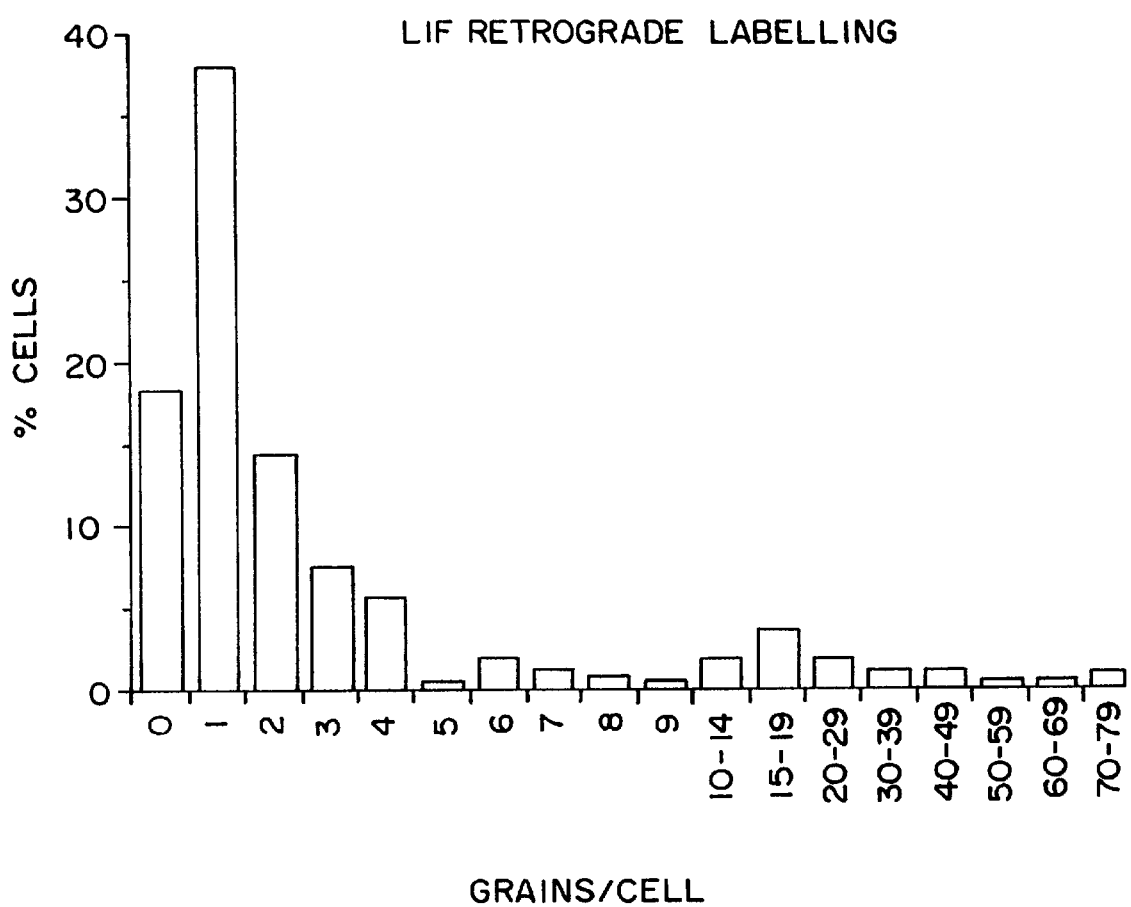
FIG. 12 is a photographic representation showing the distribution of grain counts in sections of L4 dorsal root ganglia after retrograde labelling with $^{125}$I-LIF. Note only a small proportion (5–10%) have significantly labelling.

To characterise the phenotype of neurons generated in these cultures, they were stained for the expression of markers found in sensory and autonomic neurons. All the neurons in both LIF treated and control cultures contained immunoreactivity for CGRP (FIG. 2e), the most widely expressed peptide found in mammalian sensory neurons (14,15). Limited developmental studies suggest that this peptide is expressed quite early, at least in the chick (18). Immunoreactivity for substance P, a peptide also found in mammalian sensory neurons (14,15), but only in significant level postnatally (17), was also detected in a small proportion of processes in both LIF treated and control cultures. A small proportion (1–2%) of these neurons (both LIF treated and control) had tyrosine hydroxylase activity, a marker for catecholaminergic cells (FIG. 12f). However, none of the cells showed any immunoreactivity for CHAT, a marker for cholinergic cells.

Figure 3A:
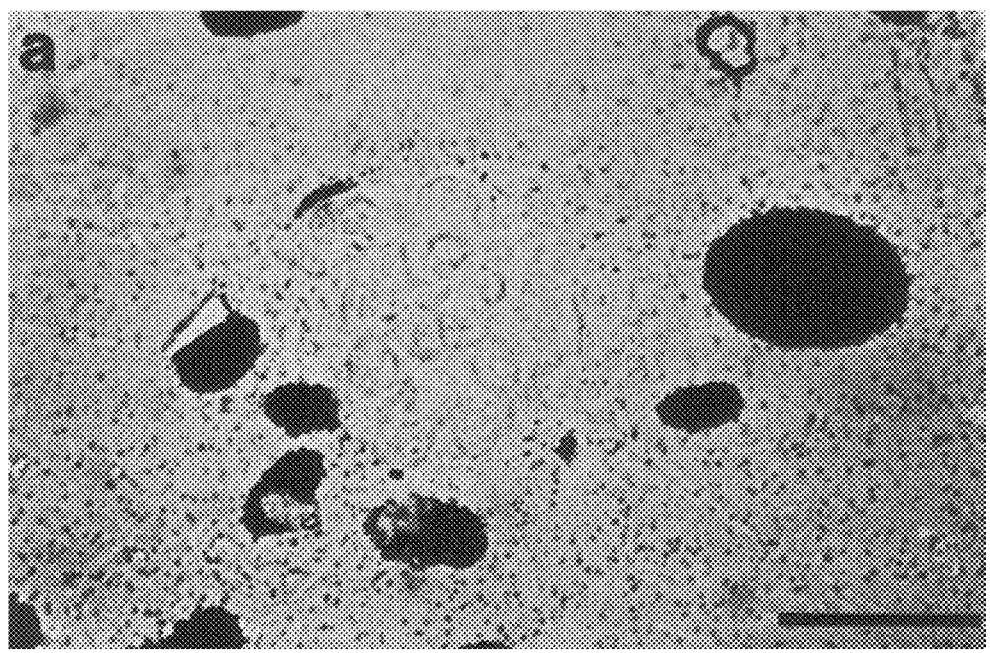
Figure 3B:
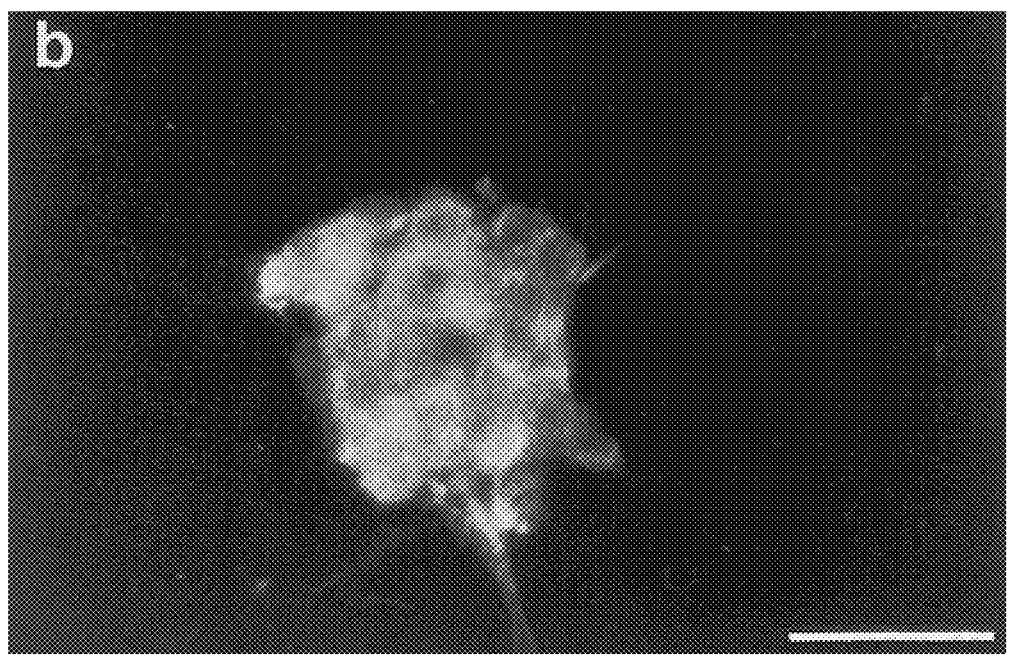

These immunohistochemical findings, as well as the morphology of the neurons, suggest that they are in the sensory lineage. Previous work in avian species has shown that at least a proportion of sensory neurons arise from non-dividing precursors in the neural crest (1–2). To investigate whether the neurons in the LIF treated cultures also arose from non-dividing precursors, $^3$H-thymidine was added to the cultures concomitantly with LIF at days 1, 4 and 7 of culture. Autoradiographic analysis at day 13 showed that less than 0.2% of the neurons (2 in 1100 neurons counted) which arose in the LIF cultures incorporated $^3$H-thymidine (FIG. 3) irrespective of time of addition. These observations show that the increase in neuron numbers does not result from stimulation of precursor division. Most of the non-neuronal cells in these cultures were labelled with $^3$H-thymidine (FIG. 3) but the presence of LIF made no significant difference to the total proportion of labelled cells: when LIF was added on day 1, 80+/-18% of the cells were labelled compared to 78+/-12% on control cultures, whereas at day 7, 70+/-1% AND 70+/-6% of all cells were labelled in the presence and absence of LIF, respectively [n=3].

Figure 4A:
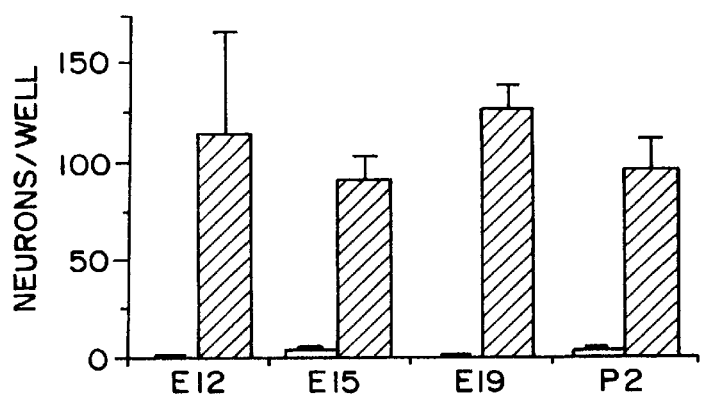

As LIF stimulates an increase in sensory-like neurons in neural crest cultures, it was anticipated to have similar activity on early embryonic DRG cultures. Thus, single cell suspensions were made from E12 DRG, which contain a subpopulation of small, probably immature neurons as well as neuronal precursors (18) and were plated into wells of HL-A plates in the presence or absence of LIF. After 3 days clusters of neuron-like cells began to appear in the LIF treated cultures, but not in control cultures. After 5 days the cultures were stained for neurofilament and neurons were counted (FIG. 4A), showing that there were approximately 100 fold more neurons in the LIF treated cultures than in controls. Neurons were also present in cultures treated with nerve growth factor (NGF), but there were only about 10% of those seen in the LIF treated cultures after 5 days. Experiments on DRG cells isolated later in development (E15, E19, P2), showed a high proportion (80–100%) of neurons survived after 2 days in the presence of LIF (FIG. 4A).

Figure 4B:
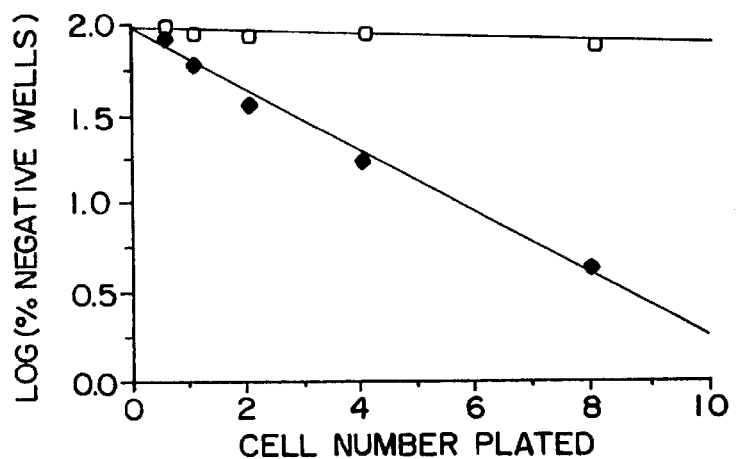
Figure 4C:
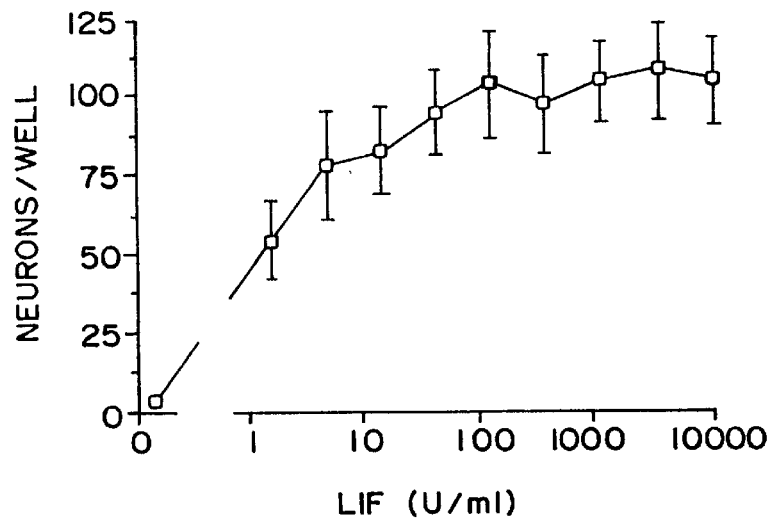

Limited dilution experiments indicate that LIF acts directly on the neurons, as the rate of survival is not influenced by cell number (FIG. 4B). In addition, a LIF titration on the P2 DRG showed maximal activity over $10^2$ U/ml and 50% activity at approximately 1.5 U/ml (FIG. 4C) which is comparable to that observed with other neurotrophic factors (4,5,6).

These results indicate that LIF can act throughout embryonic sensory neuron development in vitro. In neural crest cultures, it may act to stimulate neuronal differentiation and/or survival of the sensory precursors. Consistent with this, a subpopulation of neural crest cells was found to specifically bind 125I-LIF, indicating that they have LIF receptors. Others have implicated brain derived neurotrophic factor (BDNF) in the survival and/or differentiation of developing DRG cells. One possibility is that LIF, which is produced by mesoderm derived cells in vitro, may be produced in peripheral tissue in vivo and act in concert with the central nervous system derived BDNF in the development of the DRG.

The actions of LIF on the older DRG cultures show it to be a neurotrophic factor for sensory neurons in vitro like NGF. LIF acts as a survival agent for postnatal and embryonic sensory neurons. The results herein indicate that LIF acts not only during the critical period of target innervation of the neurons but later as well. Thus, LIF may be exerting its effects throughout the development of sensory neurons and into adulthood.

EXAMPLE 3

Effect of LIF on Spinal Cord Neurons

1. LIF Stimulates Process Outgrowth from Embryonic Spinal Cord

Figure 5A:
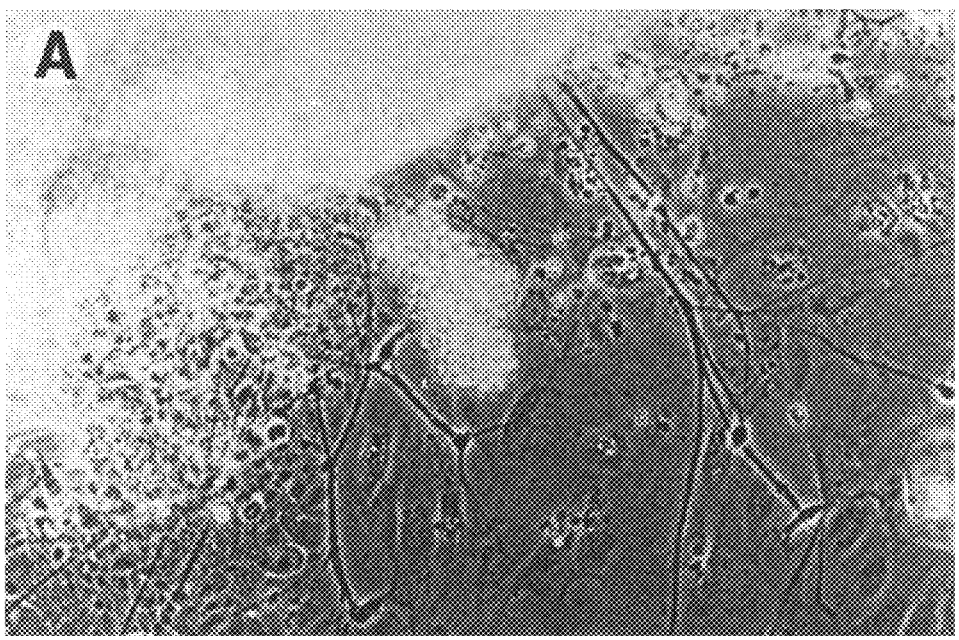
Figure 5B:
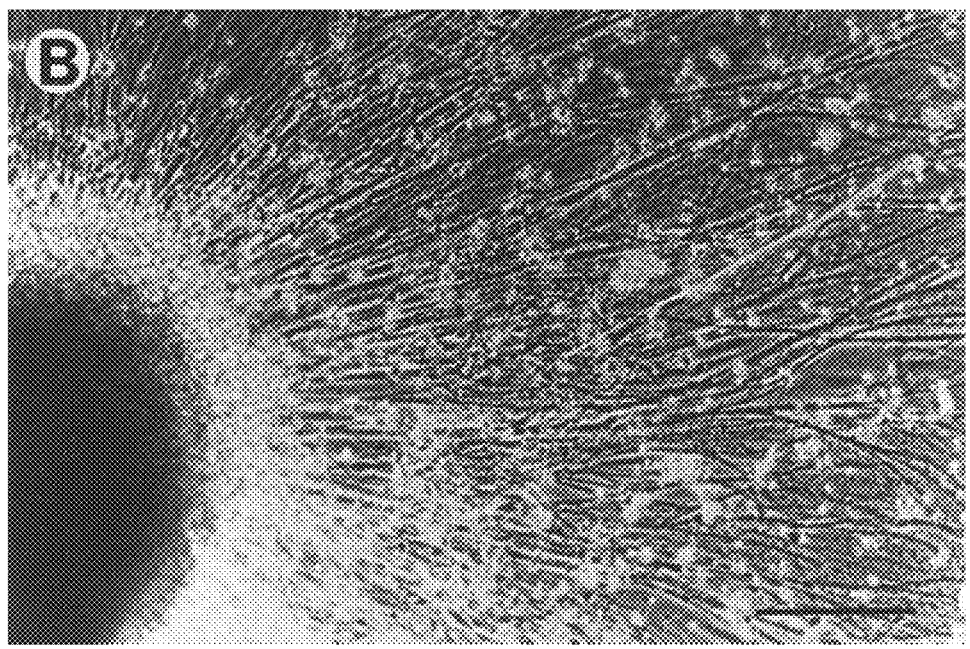
Figure 6A:
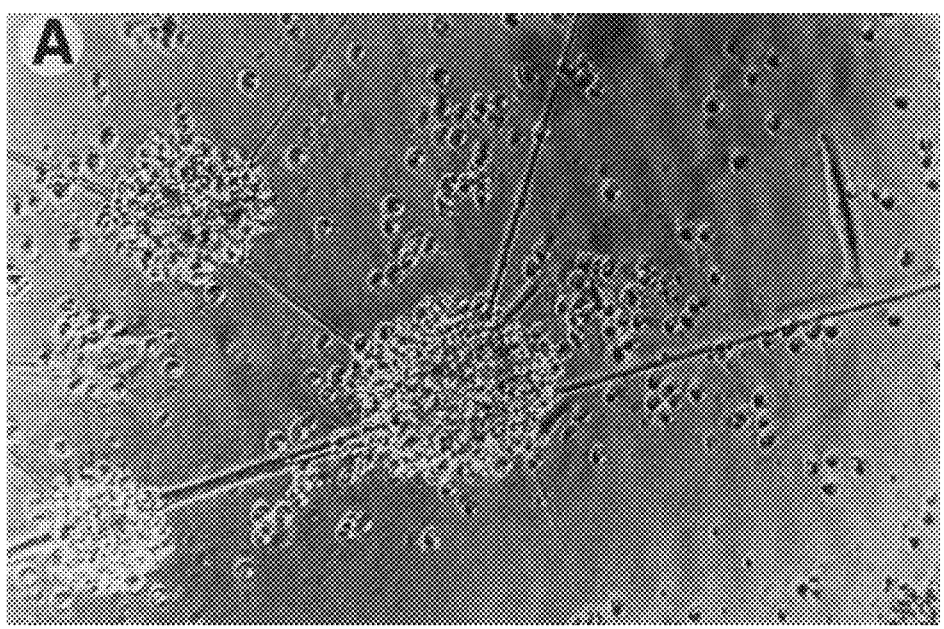
Figure 6B:
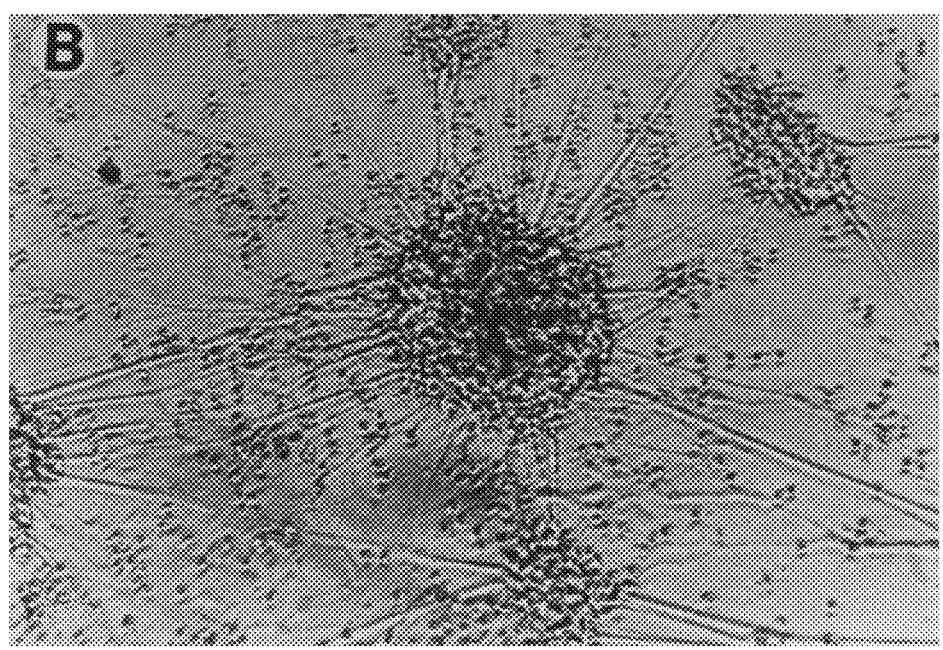
Figure 6C:
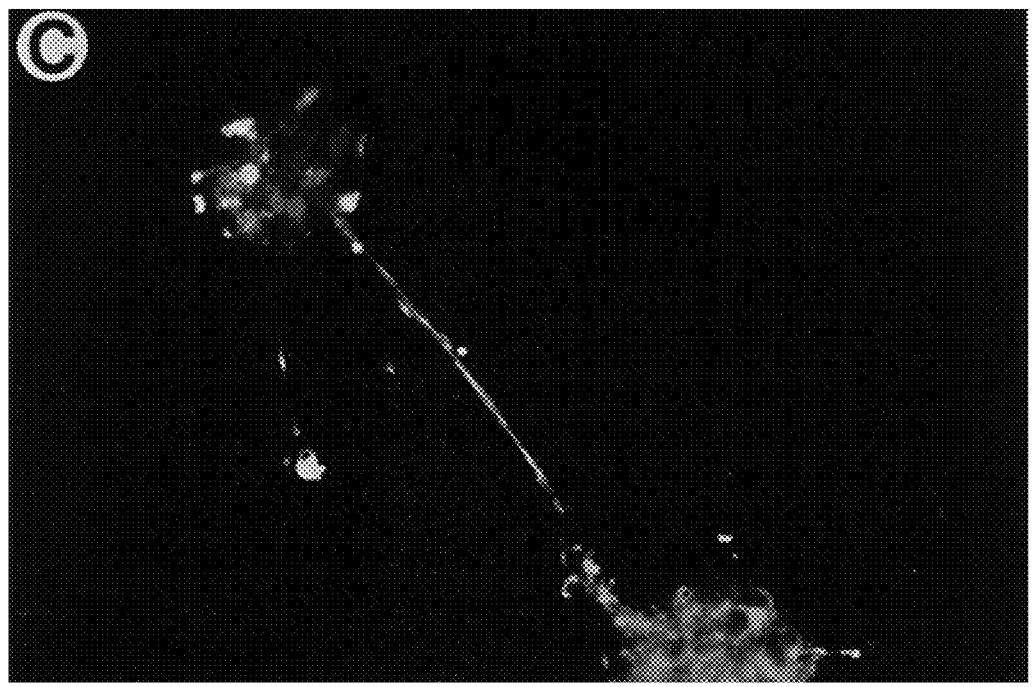
Figure 6D:
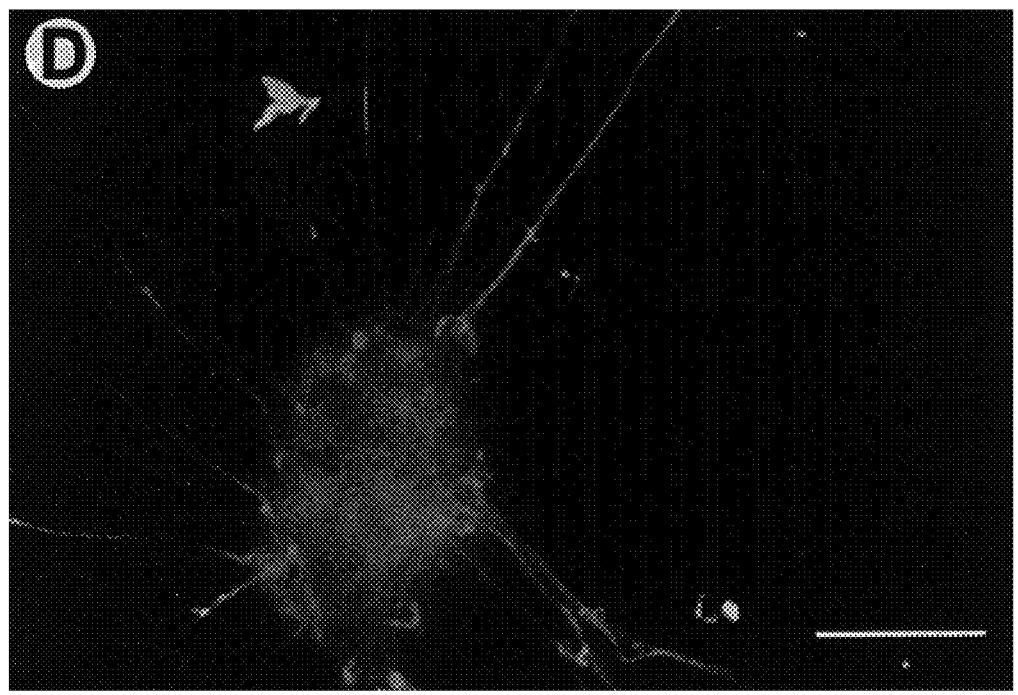

In Example 2, it was shown that LIF stimulates the development of sensory neurons in cultures of neural crest obtained from E9 mice embryos. In these cultures, the crest cells migrate out from the embryonic spinal cord onto the fibronectin substratum and the sensory neurons in the LIF cultures appear as clusters surrounding and at some distance from the spinal cord explant. It had been noted that LIF also influenced the appearance of the spinal cord where the explant had been left in the cultures increasing their apparent viability and process outgrowth. These experiments were repeated on spinal cord explants from E10 embryos, where most of the neural crest has already migrated away from the cord, but little neuronal differentiation occurred. In order to see if LIF might be acting on neurons or their precursors in the spinal cord, the serum was removed from our assays to slow down glial proliferation without necessarily affecting neuronal differentiation. As expected, in these cultures there was very little cell migration away from the explants, but there was still a great deal of process outgrowth in the LIF treated cultures (FIG. 5). The processes extended straight out from the explants, some in bundles and some as single processes, onto the substratum. There was also a limited degree of arborization of the processes. The stimulation of process outgrowth first became apparent at day 3 and increased up to a maximum at day 7.

These observations indicate that LIF may contribute to the process outgrowth and development of spinal cord neurons. To further test this, single cell suspensions of spinal cord cells were made and plated in the presence and absence of LIF to see if the effect could be observed in dissociated cultures. The advantage of these cultures is that an exact number of cells can be plated in each well as opposed to explants of different sizes and thus it may be easier to quantitate the effect of LIF.

Figure 7:
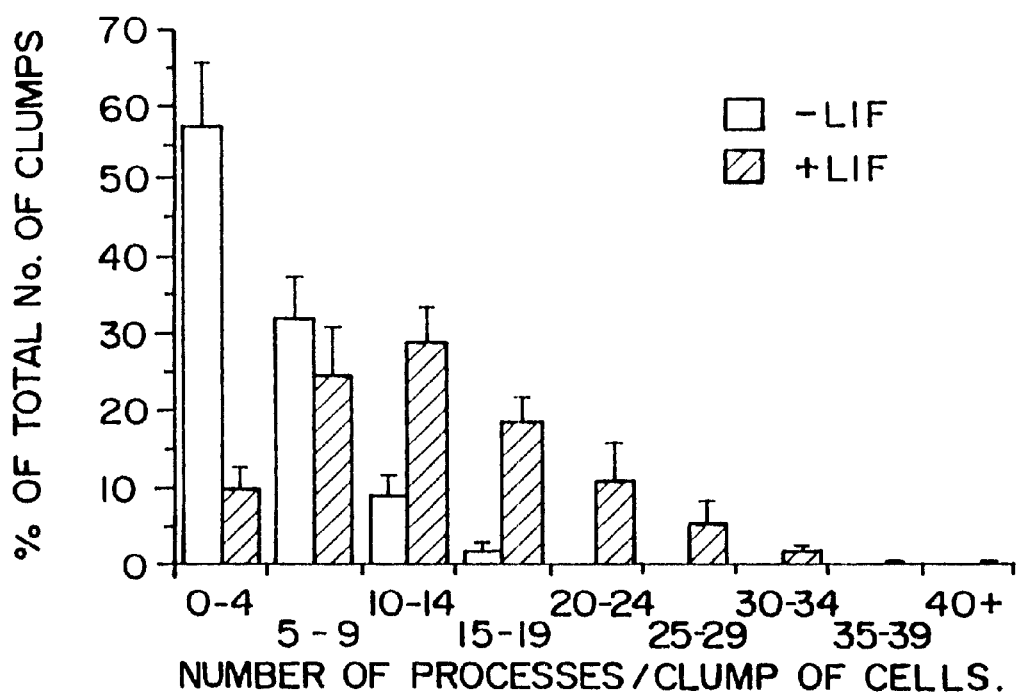

When these cells were plated at fairly high cell density in both 96 well and HLA plates, they spontaneously aggregated into discrete clusters and processes emanated from these clusters and appeared to form bridges with other clusters (FIG. 6). That these processes were definitely of neuronal origin was established by staining the cultures for neurofilament. All the processes in both LIF treated and control cultures stained positively with the anti-neurofilament antibody (FIG. 6). In the presence of LIF far more of these processes were present than in controls (FIG. 6). Almost all of the cell clusters in the LIF cultures emanated processes whereas most of the clusters in the controls had no processes. Further, there were generally more processes per cluster in the LIF cultures. This effect was observed by day 2 and was most obvious at day 5, by which time the number of processes in the control cultures had begun to diminish. At this time, the average number of processes in the LIF treated cultures was approximately 10 times that in the controls (FIG. 7).

EXAMPLE 4

LIF Stimulates an Increase in the Number of Neurons in Spinal Cord Cultures

Figure 13:
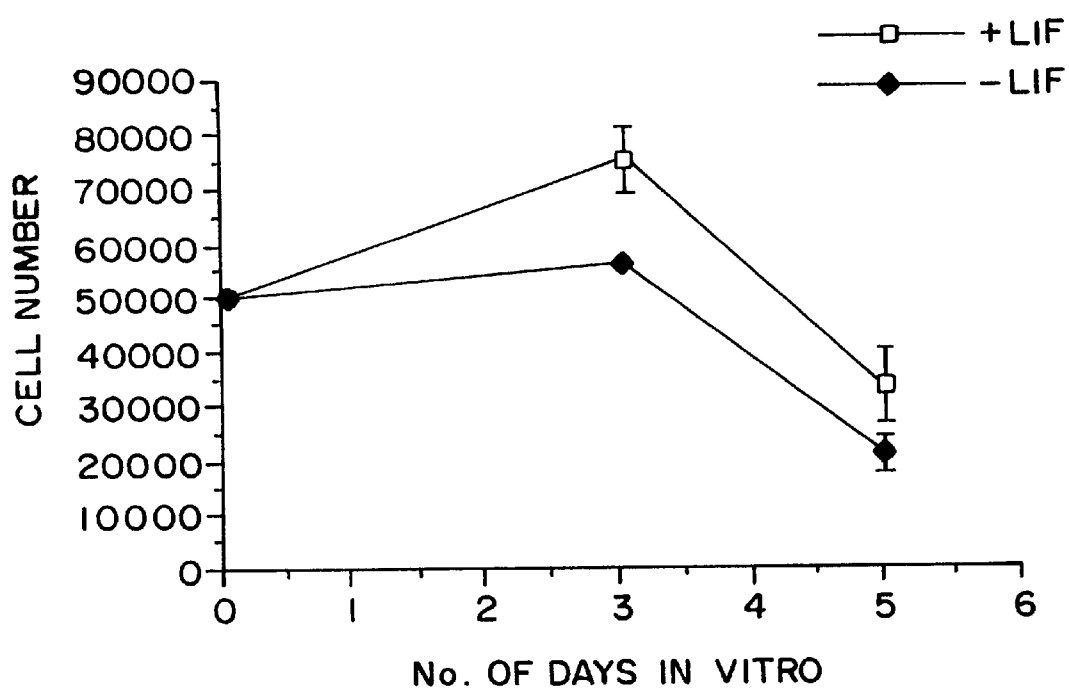
FIG. 13 is a graphical representation showing spinal cord cells surviving in vitro with and without LIF over time.

One possibility to account for the stimulation of process outgrowth by LIF is that it stimulates the survival of precursors and/or differentiation of neurons in the spinal cord cultures. Initially, the total number of cells present in the cell cultures in the presence and absence of LIF was investigated. Cell counts were performed from 96 well plates after 3 and 5 days in vitro. As shown in FIG. 13, there was a small increase in total cell numbers in the presence of LIF. These data also show that there was little increase in cell number in either LIF or control culture, suggesting that little proliferation has occurred.

The increase in numbers in the LIF cultures might either be a small survival effect or an affect on a subpopulation of cells within the culture, i.e. the neurons. However, this method of analysis does not allow for the identification of neurons in the population. To determine if there were a significant effect on neuron number, as opposed to the entire population of cells which developed in the culture system, the E10 cells were plated at low density onto irradiated Balb/c-3T3 monolayers. Under these conditions, the cultures could be stained for neurofilament and individual neurons counted. By day 4 there were approximately 2 fold more neurons in the LIF treated cultures. In culture where 10,000 spinal cord cells were plated, 1920 neurons were observed in the LIF treated cultures compared to 998 in controls. In cultures where 2500 spinal cord cells were plated, there were 625 neurons in the LIF treated cultures compated to 343 in controls. By day 7 of culture there was still good survivial of neurons in the LIF cultures, whereas almost all of the neurons had died in the control cultures. These data suggest that LIF stimulates both the differentiation and survival of spinal cord neurons.

These experiments show that LIF stimulates process outgrowth from the undifferentiated trunk neural tube and from the embryonic spinal cord. Thus, LIF appears to be acting to stimulate the differentiation of spinal neurons which innervate the peripheral tissues of the body. The three major classes of neurons which do this are the lower motor neurons of the spinal cord and the preganglionic sympathetic and parasympathetic chains. As it is not yet possible to distinguish which of these classes LIF may be effecting, it can be speculated that the lower motor neurons would be good candidates given that the processes emanating from the tube are thick and extend long distances from the neural tube. Only lower motor neurons do this in vivo from the spinal cord. In addition, LIF has been found in the muscle which is the natural target of lower motor neuron innervation. A cohesive hypothesis is that LIF is the muscle derived target factor for these motor neurons. It stimulates them to extend processes toward the target and then acts as a survival factor for the neurons which have successfully innervated the muscle.

EXAMPLE 5

Binding and Retrograde Labelling Experiments

Figure 8A:
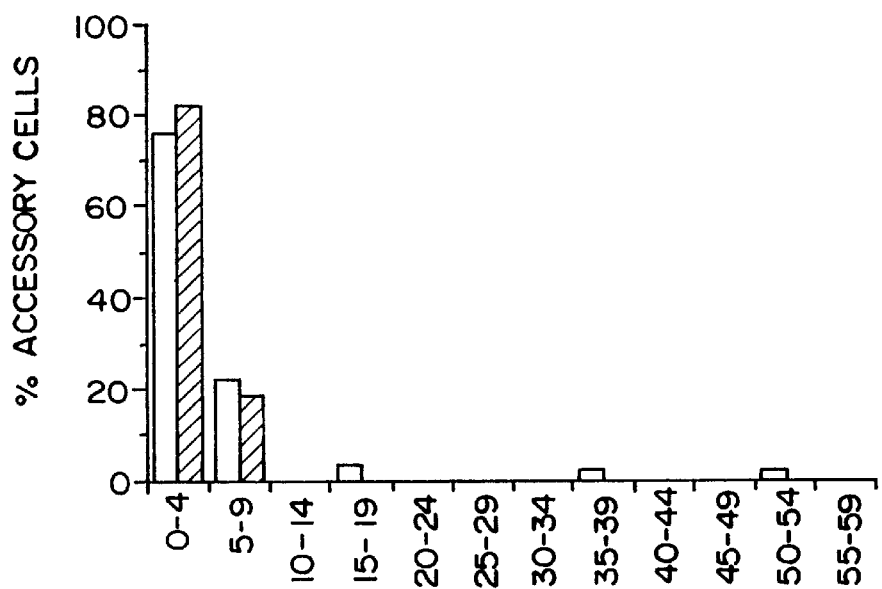
Figure 8B:
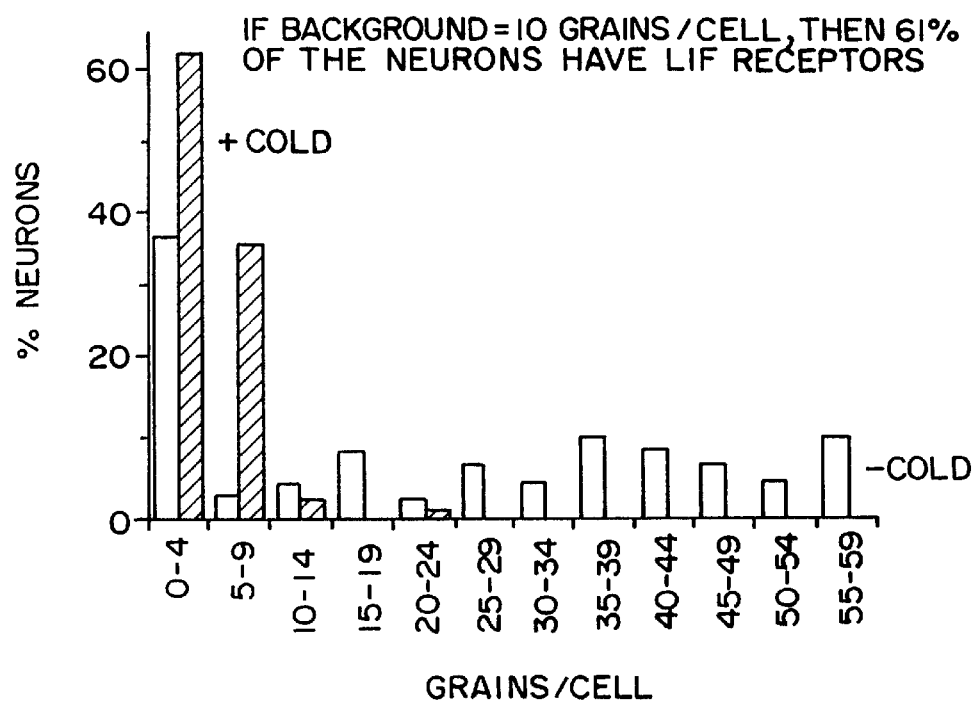

Example 2 shows that LIF supports the survival of the majority of sensory neurons form newborn dorsal root ganglia. This is evident even at very low cell numbers—single neurons could be supported—indicating that LIF probably acts directly on neurons and not via an accessory cell. To formally prove that sensory neurons express high affinity LIF receptors, binding studies on isolated sensory neurons were carried out in vitro. As shown in FIG. 8, greater than 50% of cells identified as neurons by their expression of neurofilament bound significant amounts of $^{125}$I-LIF, all of which was inhibited by the addition of cold LIF. Furthermore, there was negligible cold-inhibitable binding of $^{125}$I-LIF to non-neuronal cells in the culture.

These results show that mature sensory neurons do express high affinity receptors for LIF and that the accessory cells, such as Schwann cells, do not. This strongly argues for the direct neuronal action of LIF, which was predicted from the limiting dilution studies (Example 2) in which LIF supported the survival of very low numbers of sensory neurons. Studies with radiolabelled NGF have shown that both Schwann cells and neurons bind NGF in vitro, although it is not clear whether this reflects the steady—state in vivo situation. Apart from LIF, no other factors have been shown binding limited to the neuronal component.

The observed distribution of receptors fits well with results on in vitro survival that show that the vast majority of sensory neurons survive in the presence of LIF. The restricted distribution also suggests that LIF receptors may be limited to the neuronal lineage during sensory ganglia development.

Having demonstrated the presence of LIF receptors on sensory neurons in vitro, it was next investigated whether receptor mediated uptake of LIF would result in retrograde transport to the sensory neuron soma. Experiments using nerve ligation were carried out to determine if there was any retrograde transport of 125I-LIF by neurons with axons in the sciatic nerve. It was found that there was significant accumulation of radioactivity in the distal segment of the nerve after injection of $^{125}$I-LIF, into both the foot or leg (see Table 1). The time course of this accumulation suggested that it was due to retrograde transport and not to other mechanisms; furthermore there was no evidence of the distal accumulation of $^{125}$I-FGF after injection.

Figure 9:
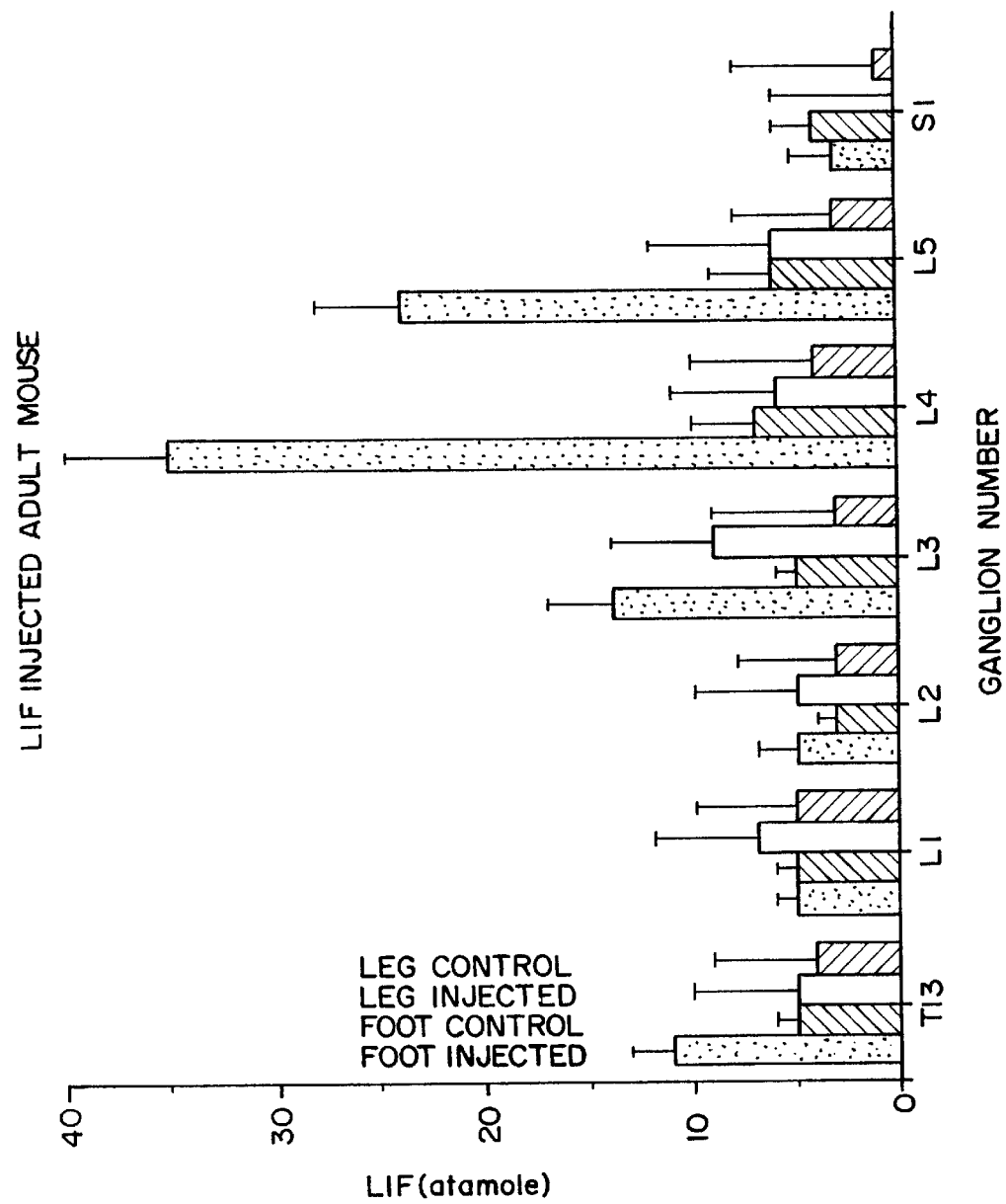

In order to examine more closely which neurons were involved in the retrograde transport of LIF, adult mice were again injected in the skin or muscle, but this time with the sciatic nerve intact. In those animals injected in the skin of the foot, after 16 hours there was a significant accumulation of radioactivity in the sensory ganglia centered on lumbar ganglion 4 (L4; FIG. 9). There was a very much smaller accumulation of radioactivity in those animals injected in the muscle and this appeared to be more rostral (FIG. 9). Although FGF has been shown to support a range of neurons, including sensory neurons, there was no evidence of accumulation of $^{125}$I-FGF in the lumbar DRG or spinal cord.

TABLE 1

Injection of LIF into adult mice with ligated sciatic nerve
Accumulation of LIF in nerve
μM/2 mm

| Time after injection | Proximal stump | Distal stump |
|---|---|---|
| Injection into footpad | | |
| 7 hrs | 0.144 ± .024 | 0.349 ± .084 |
| 16 hrs | 0.170 ± .034 | 0.777 ± .108 |
| 24 hrs | 0.060 ± .006 | 0.551 ± .045 |
| Injection into the gastrocnemius muscle | | |
| 7 hrs | 0.109 ± .008 | 0.488 ± .128 |
| 16 hrs | 0.137 ± .014 | 0.550 ± .135 |
| 24 hrs | 0.069 ± .004 | 0.399 ± .138 |

The sciatic nerve was ligated in the mid high region of the adult mice and 1 μCi of $^{125}$I-LIF was injected either into the footpad of calf. After the various times the nerve was removed and 2 mm sections either side of the ligature were taken and radioactively measured in a gamma counter.

In newborn mice there was a greater accumulation of radioactivity for both the leg and foot injections. The skin injection again was centered on L4 (FIG. 10). The transport from the muscle injection was more widespread and may reflect the greater spread from the injection site in these small animals (FIG. 10). Again in both cases the accumulation of radioactivity in the L4 ganglia followed a time course consistent with retrograde transport.

Autoradiographic examination of histological sections through L4 ganglia from both adult and newborn animals injected with $^{125}$I-LIF into the footpad has revealed the presence of radioactive material in a subpopulation of neurons (FIG. 11). The number of neurons with significant number of grains is between 5–10% of the population (FIG. 12), again there is no evidence of radioactivity associated with non-neuronal cells (FIG. 11).

A major finding in accordance with this aspect of the present invention is that LIF is retrogradely transported in a manner resembling NGF. This re-enforces the view that the expression of LIF receptors is not an in vitro artefact and more importantly implicates LIF as a neurotrophic molecule for sensory neurons. As far as the present inventors know this is the only neurotrophic molecule, outside of NGF, that has been shown to be transported in such a manner, although there is evidence that FGF can be transported antero gradely in retinal ganglion cells. LIF, like NGF, does not appear to be transported antero gradely as there is no evidence of accumulation of the molecule in the spinal cord. It appears that LIF is not transported by motor neurons in the sciatic nerve nor does it appear to be transported in the sympathetic or parasympathetic nervous systems. This probably indicates that LIF is also capable of exerting a biological effect on the nervous system by directly binding to the cell surface and not undergoing receptor mediated transport. This would appear to be the primary mode of action of LIF on a wide variety of cells which include muscle, platelets, embryonal stem cells and some haemopoietic cell lines.

Although retrograde transport of NGF seems to be required for some of its biological action, no such evidence exists for LIF. The similarities of action of the two factors in the developing sensory neurons suggests that this process may be necessary to deliver a sufficient biological signal from the periphery to the cell soma. Such a suggestion appears too simplistic given the findings that NGF injected into the cell soma does not result in neuron survival. This suggests that it is the receptor-ligand complex that is important in signal delivery.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. Le Dourin, N. M. Science 231: 1515–1522, 1986.
2. Ziller, C., Fauquet, M., Kalcheim, C., Smith, J., & Le Douarin, N. M. Dev. Biol. 120: 101–111, 1987.
3. Anderson, D. J. Neuron 3: 1–12, 1989.
4. Levi-Montalcini, R. Annu. Rev. Neurosci. 5: 341–362, 1982.
5. Barde, Y. Neuron. 2: 1525–1534, 1989.
6. Barbin, G., Manthorpe, M., & Varon, S. J. Neurochem. 43: 1468–1478, 1984.
7. Murphy, M., Drago, J. & Bartlett, P. J. Neurosci. Res. 25: 463–475, 1990.
8. Nissl, F. Allg. Z. Psychiat. 48: 197–198, 1982.
9. Good, M. F., Boyd, A. W. & Nossal, G. J. V. J. Immunol. 130: 2046–2055, 1983.
10. Eckenstein, F. P., Baughman, R. W. & Quinn, J. Neurosci. 25: 457–474, 1988.
11. Example 1, isolation of spinal cord cells.
12. Hilton et al., 1990.
13. Hilton, D,J., Nicola, N. A., & Metcalf, D. Anal. Biochem. 173: 359–367, 1988.
14. Shaw, G., Osborne, M., * Weber, H. Eur. J. Cell. Biol. 26: 68–82, 1981.
15. Ju, G., Hokfelt, T., Brodin, E., Fahrenkrug, J., Fisher, J. A., Frey, P., Elde, R. P., & Brown, J. C. Cell Tiss. Res. 247: 417–431, 1987.
16. Gibbins, I. L., Furness, J. B., & Costa, M. Cell Tiss. Res. 248: 417–437, 1987.
17. Juurlink, B. H. J., Munoz, D. G., & Devon, R. M. J. Neurosci. Res. 26: 238–241, 1990.
18. Kessler, J. A., & Black, I. B. Proc. Natl. Acad. Sci. USA 77: 649–652, 1980.
19. Lawson, S. N., Caddy, K. W. T., & Biscoe, T. J. Cell Tiss. Res. 153: 399–413, 1974.
20. Malcheim, C., & Jandreau, M. Dev. Brain Res. 41: 79–86, 1988.
21. Malcheim, C., Barde, Y. A., Thoenen, H., & Le Douarin, N. M. EMBO J. 6: 2871–2873, 1987.

What is claimed is:

1. A method for promoting the survival of mammalian sensory neurons comprising contacting said sensory neurons with a survival-promoting amount of leukemia inhibitory factor (LIF) for a time and under conditions sufficient to promote the survival of said sensory neurons.

2. The method according to claim 1 wherein the neurons are located in the peripheral nervous system.

3. The method according to claim 1 wherein the mammal is human.

4. The method according to claim 1 wherein the LIF is mammalian LIF.

5. The method according to claim 4 wherein the mammalian LIF is mouse, rat, human or livestock animal LIF.

6. The method according to claim 1 wherein the mammalian LIF and the mammalian sensory neurons belong to the same species.

7. The method according to claim 1 wherein the survival-promoting amount of LIF is from about 0.01 to about 10,000 µg/kg body weight.

8. The method according to claim 7 further comprising the simultaneous or sequential administration of one or more other neuron stimulating factors.

9. The method according to claim 8 wherein said other neuron stimulating factor is selected from the group consisting of fibroblast growth factor, ciliary neurotrophic factor, nerve growth factor, and brain-derived neurotrophic factor.

10. The method according to claim 9 wherein each other neuron stimulating factor is administered in an effective amount of from about 0.01 to about 10,000 µg/kg body weight.

* * * * *

UNITED STATES PATENT AND TRADEMARK OFFICE
CERTIFICATE OF CORRECTION

| | | |
|---|---|---|
| PATENT NO. | : 6,177,402 B1 | Page 1 of 1 |
| APPLICATION NO. | : 08/410402 | |
| DATED | : January 23, 2001 | |
| INVENTOR(S) | : Perry Bartlett et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

This patent is subject to a terminal disclaimer.

Signed and Sealed this
Eleventh Day of October, 2011

David J. Kappos
*Director of the United States Patent and Trademark Office*